United States Patent
Sakuraba et al.

(10) Patent No.: US 8,668,907 B2
(45) Date of Patent: *Mar. 11, 2014

(54) HIGHLY FUNCTIONAL ENZYME HAVING α-GALACTOSIDASE ACTIVITY

(71) Applicants: Tokyo Metropolitan Organization for Medical Science, Tokyo (JP); Altif Laboratories, Tokyo (JP)

(72) Inventors: Hitoshi Sakuraba, Tokyo (JP); Youichi Tajima, Tokyo (JP); Mai Ito, Tokyo (JP); Seiichi Aikawa, Tokyo (JP); Fumiko Aikawa, Tokyo (JP)

(73) Assignees: Tokyo Metropolitan Institute of Medical Science, Setagaya-Ku, Tokyo (JP); Altif Laboratories, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/667,294

(22) Filed: Nov. 2, 2012

(65) Prior Publication Data

US 2013/0064805 A1 Mar. 14, 2013

Related U.S. Application Data

(62) Division of application No. 13/052,632, filed on Mar. 21, 2011, now Pat. No. 8,323,640, which is a division of application No. 12/084,982, filed as application No. PCT/JP2006/323509 on Nov. 17, 2006, now Pat. No. 7,935,336.

(30) Foreign Application Priority Data

Nov. 18, 2005 (JP) ................... 2005-333660

(51) Int. Cl.
*A61K 38/43* (2006.01)
*A61K 38/47* (2006.01)
*C12N 9/40* (2006.01)
*C12P 21/06* (2006.01)
*C07H 21/04* (2006.01)
*C07K 1/00* (2006.01)

(52) U.S. Cl.
USPC ...... 424/94.1; 424/94.61; 435/208; 435/69.1; 536/23.2; 530/350

(58) Field of Classification Search
USPC .................... 424/94.1, 94.61; 435/208, 69.1; 536/23.2; 530/350
See application file for complete search history.

(56) References Cited

U.S. PATENT DOCUMENTS

| | | | |
|---|---|---|---|
| 5,356,804 A | 10/1994 | Desnick et al. | |
| 5,401,650 A | 3/1995 | Desnick et al. | |
| 6,887,696 B2 | 5/2005 | Garger et al. | |
| 6,890,748 B2 | 5/2005 | Garger et al. | |
| 7,011,831 B2 * | 3/2006 | Calhoun et al. | 424/94.61 |
| 7,935,336 B2 | 5/2011 | Sakuraba et al. | |
| 8,323,640 B2 * | 12/2012 | Sakuraba et al. | 424/94.1 |
| 2003/0077806 A1 | 4/2003 | Selden et al. | |
| 2010/0291059 A1 | 11/2010 | Sakuraba et al. | |

FOREIGN PATENT DOCUMENTS

JP  2001-504324 A  4/2001

OTHER PUBLICATIONS

Broun et al.; Catalytic Plasticity of Fatty Acid Modification Enzymes Underlying Chemical Diversity of Plant Lipids. Science, vol. 282, 1998, pp. 1315-1317.
Cameron ER., Recent Advances in Transgenic Technology. Molecular Biology, vol. 7, 1997, pp. 253-265.
Chica et al., Semi-Rational Approaches to Engineering Enzyme Activity: Combining the Benefits of Directed Evolution and Rational Design. Current Opinion in Biotechnology, vol. 16, 2005, pp. 378-384.
Couzin et al., As Gelsinger Case Ends, Gene Therapy Suffers Another Blow. Science, vol. 307, Feb. 18, 2005, p. 1028.
Devos et al., Practical Limits of Function Prediction. Proteins: Structure, Function, and Genetics. vol. 41, 2000, pp. 98-107.
Donsante et al., AAV Vector Integration Sites in Mouse Hepatocellular Carcinoma. Science, vol. 317, Jul. 27, 2007, p. 477.
Juengst, E.T., What Next for Human Gene Therapy? BMJ, vol. 326, Jun. 28, 2003, pp. 1410-1411.
Kappel et al., Regulating Gene Expression in Transgenic Animals. Current Opinion in Biotechnology, vol. 3, 1992, pp. 548-553.
Kimmelman, J., Recent Developments in Gene Transfer: Risk and Ethics. BMJ, vol. 330, Jan. 8, 2005, pp. 79-82.
Kisselev, L., Polypeptide Release Factors in Prokaryotes and Eukaryotes: Same Function, Different Structure. Structure, vol. 10, 2002, pp. 8-9.
Mullins et al., Transgenesis in the Rat and Larger Mammals. Journal of Clinical Investigation, vol. 97, No. 7, Apr. 1996, pp. 1557-1560.
Mullins et al., Transgenesis in Nonmurine Species. Hypertension, vol. 22 (4), 1993, pp. 630-633.
Raper, S.E., Gene therapy: The Good, the Bad, and the Ugly, Surgery, vol. 137 (5), May 2005, pp. 487-492.

(Continued)

*Primary Examiner* — Ganapathirama Raghu
(74) *Attorney, Agent, or Firm* — Westerman, Hattori, Daniels & Adrian, LLP

(57) ABSTRACT

The present invention provides, as an enzyme which can be used for enzyme replacement therapy for Fabry disease, a protein having α-galactosidase activity, which shows no allergic adverse side effect, shows a high stability in blood, and can be easily incorporated into a cell of an affected organ. The protein of the present invention is a protein which has acquired α-galactosidase activity by changing the structure of the active site of wild-type human α-N-acetylgalactosaminidase.

6 Claims, 9 Drawing Sheets

(56) References Cited

OTHER PUBLICATIONS

Rosenberg et al., Gene Therapist, Heal Thyself. Science, vol. 287, Mar. 10, 2000, p. 1751.
Sen et al., Developments in Directed Evolution for Improving Enzyme Functions. Applied Biochemistry and Biotechnology, vol. 143, Aug. 18, 2007, pp. 212-233.
Touchette et al., Gene Therapy: Not Ready for Prime Time. Nature Medicine, vol. 2 (1), Jan. 1, 1996, pp. 7-8.
Whisstock et al., Prediction of Protein Function from Protein Sequence. Quarterly Reviews of Biophysics vol. 36 (3), 2003, pp. 307-340.
Wigley et al., Site-Specific Transgene Insertion: an Approach. Reproduction, Fertility, and Development, vol. 6, 1994, pp. 585-588.
Wishart et al., A Single Mutation Converts a Novel Phosphotyrosine Binding Domain into a Dual-Specificity Phosphatase. Journal of Biological Chemistry vol. 270 (45), Nov. 10, 1995, pp. 26782-26785.
Witkowski et al., Conversion of β-Ketoacyl Synthase to a Malonyl Decarboxylase by Replacement of the Active Cysteine with Glutamine. Biochemistry, vol. 38, 1999, pp. 11643-11650.
Wolff JA. The "Grand" Problem of Synthetic Delivery. National Biotechnology, vol. 20, Aug. 2002, pp. 768-769.
Database UniProt Aug. 11, 2005, XP002512954 Database accession No. AEA27443.
Database UniProt, Dec. 1, 2001, XP002512955, Database accession No. P51569.
European Search Report dated Feb. 17, 2009, issued in corresponding European Patent Application No. 06833313.
Garman, S.C. et al., Structural Basis of Fabry Disease. Molecular Genetics and Metabolism, vol. 77, No. 1-2, 2002, pp. 3-11.
Garman, S.C. et al., The 1.9 Å Structure of α-N-Acetylgalactosaminidase: Molecular Basis of Glycosidase Deficiency Diseases. Structure, vol. 10, No. 3, Mar. 2002, pp. 425-434.
Garman, S.C. et al., The Molecular Defect Leading to Fabry Disease: Structure of Human α-Galactosidase. Journal of Molecular Biology, vol. 337, No. 2, 2004, pp. 319-335.
International Search Report of PCT/JP2006/323509, date of mailing Feb. 13, 2007.

\* cited by examiner

SEQUENCE LISTING

<160> NUMBER OF SEQ ID NOS: 15

<210> SEQ ID NO 1
<211> LENGTH: 1236
<212> TYPE: DNA
<213> ORGANISM: homo sapiens
<220> FEATURE:
<221> NAME/KEY: CDS
<222> LOCATION: (1)..(1236)

<400> SEQUENCE: 1

```
atg ctg ctg aag aca gtg ctc ttg ctg gga cat gtg gcc cag gtg ctg       48
Met Leu Leu Lys Thr Val Leu Leu Leu Gly His Val Ala Gln Val Leu
1               5                   10                  15 atg ctg gac aat ggg ctc ctg cag aca cca ccc atg ggc tgg ctg gcc       96
Met Leu Asp Asn Gly Leu Leu Gln Thr Pro Pro Met Gly Trp Leu Ala
            20                  25                  30 tgg gaa cgc ttc cgc tgc aac att aac tgt gat gag gac cca aag aac      144
Trp Glu Arg Phe Arg Cys Asn Ile Asn Cys Asp Glu Asp Pro Lys Asn
        35                  40                  45 tgc ata agt gaa cag ctc ttc atg gag atg gct gac cgg atg gca cag      192
Cys Ile Ser Glu Gln Leu Phe Met Glu Met Ala Asp Arg Met Ala Gln
    50                  55                  60 gat gga tgg cgg gac atg ggc tac aca tac cta aac att gat gac tgc      240
Asp Gly Trp Arg Asp Met Gly Tyr Thr Tyr Leu Asn Ile Asp Asp Cys
65                  70                  75                  80 tgg atc ggc ggt cgc gat gcc agt ggc cgc ctg atg cca gat ccc aag      288
Trp Ile Gly Gly Arg Asp Ala Ser Gly Arg Leu Met Pro Asp Pro Lys
                85                  90                  95 cgc ttc cct cat ggc att cct ttc ctg gct gac tac gtt cac tcc ctg      336
Arg Phe Pro His Gly Ile Pro Phe Leu Ala Asp Tyr Val His Ser Leu
            100                 105                 110 ggc ctg aag ttg ggt atc tac gcg gac atg ggc aac ttc acc tgc atg      384
Gly Leu Lys Leu Gly Ile Tyr Ala Asp Met Gly Asn Phe Thr Cys Met
        115                 120                 125 ggt tac cca ggc acc aca ctg gac aag gtg gtc cag gat gct cag acc      432
Gly Tyr Pro Gly Thr Thr Leu Asp Lys Val Val Gln Asp Ala Gln Thr
    130                 135                 140 ttc gcc gag tgg aag gta gac atg ctc aag ctg gat ggc tgc ttc tcc      480
Phe Ala Glu Trp Lys Val Asp Met Leu Lys Leu Asp Gly Cys Phe Ser
145                 150                 155                 160 acc ccc gag gag cgg gcc cag ggg tac ccc aag atg gct gct gcc ctg      528
Thr Pro Glu Glu Arg Ala Gln Gly Tyr Pro Lys Met Ala Ala Ala Leu
                165                 170                 175 aat gcc aca ggc cgc ccc atc gcc ttc tcc tgc agc tgg cca gcc tat      576
Asn Ala Thr Gly Arg Pro Ile Ala Phe Ser Cys Ser Trp Pro Ala Tyr
            180                 185                 190 gaa ggc ggc ctc ccc cca agg gtg aac tac agt ctg ctg gcg gac atc      624
Glu Gly Gly Leu Pro Pro Arg Val Asn Tyr Ser Leu Leu Ala Asp Ile
        195                 200                 205 tgc aac ctc tgg cgt aac tat gat gac atc cag gac tcc tgg tgg agc      672
Cys Asn Leu Trp Arg Asn Tyr Asp Asp Ile Gln Asp Ser Trp Trp Ser
```

```
                210               215              220
gtg ctc tcc atc ctg aat tgg ttc gtg gag cac cag gac ata ctg cag    720
Val Leu Ser Ile Leu Asn Trp Phe Val Glu His Gln Asp Ile Leu Gln
225                 230                 235                 240 cca gtg gcc ggc cct ggg cac tgg aat gac cct gac atg ctg ctc att    768
Pro Val Ala Gly Pro Gly His Trp Asn Asp Pro Asp Met Leu Leu Ile
            245                 250                 255 ggg aac ttt ggt ctc agc tta gag caa tcc cgg gcc cag atg gcc ctg    816
Gly Asn Phe Gly Leu Ser Leu Glu Gln Ser Arg Ala Gln Met Ala Leu
        260                 265                 270 tgg acg gtg ctg gca gcc ccc ctc ttg atg tcc aca gac ctg cgt acc    864
Trp Thr Val Leu Ala Ala Pro Leu Leu Met Ser Thr Asp Leu Arg Thr
    275                 280                 285 atc tcc gcc cag aac atg gac att ctg cag aat cca ctc atg atc aaa    912
Ile Ser Ala Gln Asn Met Asp Ile Leu Gln Asn Pro Leu Met Ile Lys
290                 295                 300 atc aac cag gat ccc tta ggc atc cag gga cgc agg att cac aag gaa    960
Ile Asn Gln Asp Pro Leu Gly Ile Gln Gly Arg Arg Ile His Lys Glu
305                 310                 315                 320 aaa tct ctc atc gaa gtg tac atg cgg cct ctg tcc aac aag gct agc    1008
Lys Ser Leu Ile Glu Val Tyr Met Arg Pro Leu Ser Asn Lys Ala Ser
            325                 330                 335 gcc tta gtc ttc ttc agc tgc agg acc gat atg cct tat cgc tac cac    1056
Ala Leu Val Phe Phe Ser Cys Arg Thr Asp Met Pro Tyr Arg Tyr His
        340                 345                 350 tcc tcc ctt ggc cag ctg aac ttc acc ggg tct gtg ata tat gag gcc    1104
Ser Ser Leu Gly Gln Leu Asn Phe Thr Gly Ser Val Ile Tyr Glu Ala
    355                 360                 365 cag gac gtc tac tca ggt gac atc atc agt ggc ctc cga gat gaa acc    1152
Gln Asp Val Tyr Ser Gly Asp Ile Ile Ser Gly Leu Arg Asp Glu Thr
370                 375                 380 aac ttc aca gtg atc atc aac cct tca ggg gta gtg atg tgg tac ctg    1200
Asn Phe Thr Val Ile Ile Asn Pro Ser Gly Val Val Met Trp Tyr Leu
385                 390                 395                 400 tat ccc atc aag aac ctg gag atg tcc cag cag tga                    1236
Tyr Pro Ile Lys Asn Leu Glu Met Ser Gln Gln
            405                 410

<210> SEQ ID NO 2
<211> LENGTH: 411
<212> TYPE: PRT
<213> ORGANISM: homo sapiens

<400> SEQUENCE: 2

Met Leu Leu Lys Thr Val Leu Leu Gly His Val Ala Gln Val Leu
1               5                   10                  15

Met Leu Asp Asn Gly Leu Leu Gln Thr Pro Met Gly Trp Leu Ala
            20                  25                  30

Trp Glu Arg Phe Arg Cys Asn Ile Asn Cys Asp Glu Asp Pro Lys Asn
        35                  40                  45

Cys Ile Ser Glu Gln Leu Phe Met Glu Met Ala Asp Arg Met Ala Gln
50                  55                  60

Asp Gly Trp Arg Asp Met Gly Tyr Thr Tyr Leu Asn Ile Asp Asp Cys
65                  70                  75                  80

Trp Ile Gly Gly Arg Asp Ala Ser Gly Arg Leu Met Pro Asp Pro Lys
                85                  90                  95

Arg Phe Pro His Gly Ile Pro Phe Leu Ala Asp Tyr Val His Ser Leu
            100                 105                 110

Gly Leu Lys Leu Gly Ile Tyr Ala Asp Met Gly Asn Phe Thr Cys Met
```

```
                115                 120                 125
Gly Tyr Pro Gly Thr Thr Leu Asp Lys Val Val Gln Asp Ala Gln Thr
        130                 135                 140

Phe Ala Glu Trp Lys Val Asp Met Leu Lys Leu Asp Gly Cys Phe Ser
145                 150                 155                 160

Thr Pro Glu Glu Arg Ala Gln Gly Tyr Pro Lys Met Ala Ala Ala Leu
                165                 170                 175

Asn Ala Thr Gly Arg Pro Ile Ala Phe Ser Cys Ser Trp Pro Ala Tyr
            180                 185                 190

Glu Gly Gly Leu Pro Pro Arg Val Asn Tyr Ser Leu Leu Ala Asp Ile
        195                 200                 205

Cys Asn Leu Trp Arg Asn Tyr Asp Asp Ile Gln Asp Ser Trp Trp Ser
    210                 215                 220

Val Leu Ser Ile Leu Asn Trp Phe Val Glu His Gln Asp Ile Leu Gln
225                 230                 235                 240

Pro Val Ala Gly Pro Gly His Trp Asn Asp Pro Asp Met Leu Leu Ile
                245                 250                 255

Gly Asn Phe Gly Leu Ser Leu Glu Gln Ser Arg Ala Gln Met Ala Leu
            260                 265                 270

Trp Thr Val Leu Ala Ala Pro Leu Leu Met Ser Thr Asp Leu Arg Thr
        275                 280                 285

Ile Ser Ala Gln Asn Met Asp Ile Leu Gln Asn Pro Leu Met Ile Lys
    290                 295                 300

Ile Asn Gln Asp Pro Leu Gly Ile Gln Gly Arg Arg Ile His Lys Glu
305                 310                 315                 320

Lys Ser Leu Ile Glu Val Tyr Met Arg Pro Leu Ser Asn Lys Ala Ser
                325                 330                 335

Ala Leu Val Phe Phe Ser Cys Arg Thr Asp Met Pro Tyr Arg Tyr His
            340                 345                 350

Ser Ser Leu Gly Gln Leu Asn Phe Thr Gly Ser Val Ile Tyr Glu Ala
        355                 360                 365

Gln Asp Val Tyr Ser Gly Asp Ile Ile Ser Gly Leu Arg Asp Glu Thr
    370                 375                 380

Asn Phe Thr Val Ile Ile Asn Pro Ser Gly Val Val Met Trp Tyr Leu
385                 390                 395                 400

Tyr Pro Ile Lys Asn Leu Glu Met Ser Gln Gln
                405                 410

<210> SEQ ID NO 3
<211> LENGTH: 1236
<212> TYPE: DNA
<213> ORGANISM: Artificial Sequence
<220> FEATURE:
<223> OTHER INFORMATION: recombinant DNA where 562nd to 564th bases of
      wild type alpha-NAGA are replaced with bases representing a codon
      of glutamic acid and where 571st to 573rd bases of wild type
      alpha-NAGA are replaced with bases representing a codon of leucine
<220> FEATURE:
<221> NAME/KEY: CDS
<222> LOCATION: (1)..(1236)

<400> SEQUENCE: 3 atg ctg ctg aag aca gtg ctc ttg ctg gga cat gtg gcc cag gtg ctg      48
Met Leu Leu Lys Thr Val Leu Leu Leu Gly His Val Ala Gln Val Leu
1               5                   10                  15 atg ctg gac aat ggg ctc ctg cag aca cca ccc atg ggc tgg ctg gcc      96
Met Leu Asp Asn Gly Leu Leu Gln Thr Pro Pro Met Gly Trp Leu Ala
            20                  25                  30
```

| | | | | | | | | | | | | | | | |
|---|---|---|---|---|---|---|---|---|---|---|---|---|---|---|---|
| tgg | gaa | cgc | ttc | cgc | tgc | aac | att | aac | tgt | gat | gag | gac | cca | aag | aac | 144 |
| Trp | Glu | Arg | Phe | Arg | Cys | Asn | Ile | Asn | Cys | Asp | Glu | Asp | Pro | Lys | Asn | |
| | 35 | | | | 40 | | | | | 45 | | | | | | |

| tgc | ata | agt | gaa | cag | ctc | ttc | atg | gag | atg | gct | gac | cgg | atg | gca | cag | 192 |
|---|---|---|---|---|---|---|---|---|---|---|---|---|---|---|---|---|
| Cys | Ile | Ser | Glu | Gln | Leu | Phe | Met | Glu | Met | Ala | Asp | Arg | Met | Ala | Gln | |
| 50 | | | | | 55 | | | | | 60 | | | | | | |

| gat | gga | tgg | cgg | gac | atg | ggc | tac | aca | tac | cta | aac | att | gat | gac | tgc | 240 |
|---|---|---|---|---|---|---|---|---|---|---|---|---|---|---|---|---|
| Asp | Gly | Trp | Arg | Asp | Met | Gly | Tyr | Thr | Tyr | Leu | Asn | Ile | Asp | Asp | Cys | |
| 65 | | | | 70 | | | | | 75 | | | | | 80 | | |

| tgg | atc | ggc | ggt | cgc | gat | gcc | agt | ggc | cgc | ctg | atg | cca | gat | ccc | aag | 288 |
|---|---|---|---|---|---|---|---|---|---|---|---|---|---|---|---|---|
| Trp | Ile | Gly | Gly | Arg | Asp | Ala | Ser | Gly | Arg | Leu | Met | Pro | Asp | Pro | Lys | |
| | | | | 85 | | | | | 90 | | | | | 95 | | |

| cgc | ttc | cct | cat | ggc | att | cct | ttc | ctg | gct | gac | tac | gtt | cac | tcc | ctg | 336 |
|---|---|---|---|---|---|---|---|---|---|---|---|---|---|---|---|---|
| Arg | Phe | Pro | His | Gly | Ile | Pro | Phe | Leu | Ala | Asp | Tyr | Val | His | Ser | Leu | |
| | | | 100 | | | | | 105 | | | | | 110 | | | |

| ggc | ctg | aag | ttg | ggt | atc | tac | gcg | gac | atg | ggc | aac | ttc | acc | tgc | atg | 384 |
|---|---|---|---|---|---|---|---|---|---|---|---|---|---|---|---|---|
| Gly | Leu | Lys | Leu | Gly | Ile | Tyr | Ala | Asp | Met | Gly | Asn | Phe | Thr | Cys | Met | |
| | | 115 | | | | | 120 | | | | | 125 | | | | |

| ggt | tac | cca | ggc | acc | aca | ctg | gac | aag | gtg | gtc | cag | gat | gct | cag | acc | 432 |
|---|---|---|---|---|---|---|---|---|---|---|---|---|---|---|---|---|
| Gly | Tyr | Pro | Gly | Thr | Thr | Leu | Asp | Lys | Val | Val | Gln | Asp | Ala | Gln | Thr | |
| | 130 | | | | | 135 | | | | | 140 | | | | | |

| ttc | gcc | gag | tgg | aag | gta | gac | atg | ctc | aag | ctg | gat | ggc | tgc | ttc | tcc | 480 |
|---|---|---|---|---|---|---|---|---|---|---|---|---|---|---|---|---|
| Phe | Ala | Glu | Trp | Lys | Val | Asp | Met | Leu | Lys | Leu | Asp | Gly | Cys | Phe | Ser | |
| 145 | | | | | 150 | | | | | 155 | | | | | 160 | |

| acc | ccc | gag | gag | cgg | gcc | cag | ggg | tac | ccc | aag | atg | gct | gct | gcc | ctg | 528 |
|---|---|---|---|---|---|---|---|---|---|---|---|---|---|---|---|---|
| Thr | Pro | Glu | Glu | Arg | Ala | Gln | Gly | Tyr | Pro | Lys | Met | Ala | Ala | Ala | Leu | |
| | | | | 165 | | | | | 170 | | | | | 175 | | |

| aat | gcc | aca | ggc | cgc | ccc | atc | gcc | ttc | tcc | tgc | gag | tgg | cca | ctc | tat | 576 |
|---|---|---|---|---|---|---|---|---|---|---|---|---|---|---|---|---|
| Asn | Ala | Thr | Gly | Arg | Pro | Ile | Ala | Phe | Ser | Cys | Glu | Trp | Pro | Leu | Tyr | |
| | | | 180 | | | | | 185 | | | | | 190 | | | |

| gaa | ggc | ggc | ctc | ccc | cca | agg | gtg | aac | tac | agt | ctg | ctg | gcg | gac | atc | 624 |
|---|---|---|---|---|---|---|---|---|---|---|---|---|---|---|---|---|
| Glu | Gly | Gly | Leu | Pro | Pro | Arg | Val | Asn | Tyr | Ser | Leu | Leu | Ala | Asp | Ile | |
| | | 195 | | | | | 200 | | | | | 205 | | | | |

| tgc | aac | ctc | tgg | cgt | aac | tat | gat | gac | atc | cag | gac | tcc | tgg | tgg | agc | 672 |
|---|---|---|---|---|---|---|---|---|---|---|---|---|---|---|---|---|
| Cys | Asn | Leu | Trp | Arg | Asn | Tyr | Asp | Asp | Ile | Gln | Asp | Ser | Trp | Trp | Ser | |
| | 210 | | | | | 215 | | | | | 220 | | | | | |

| gtg | ctc | tcc | atc | ctg | aat | tgg | ttc | gtg | gag | cac | cag | gac | ata | ctg | cag | 720 |
|---|---|---|---|---|---|---|---|---|---|---|---|---|---|---|---|---|
| Val | Leu | Ser | Ile | Leu | Asn | Trp | Phe | Val | Glu | His | Gln | Asp | Ile | Leu | Gln | |
| 225 | | | | | 230 | | | | | 235 | | | | | 240 | |

| cca | gtg | gcc | ggc | cct | ggg | cac | tgg | aat | gac | cct | gac | atg | ctg | ctc | att | 768 |
|---|---|---|---|---|---|---|---|---|---|---|---|---|---|---|---|---|
| Pro | Val | Ala | Gly | Pro | Gly | His | Trp | Asn | Asp | Pro | Asp | Met | Leu | Leu | Ile | |
| | | | | 245 | | | | | 250 | | | | | 255 | | |

| ggg | aac | ttt | ggt | ctc | agc | tta | gag | caa | tcc | cgg | gcc | cag | atg | gcc | ctg | 816 |
|---|---|---|---|---|---|---|---|---|---|---|---|---|---|---|---|---|
| Gly | Asn | Phe | Gly | Leu | Ser | Leu | Glu | Gln | Ser | Arg | Ala | Gln | Met | Ala | Leu | |
| | | | | 260 | | | | | 265 | | | | | 270 | | |

| tgg | acg | gtg | ctg | gca | gcc | ccc | ctc | ttg | atg | tcc | aca | gac | ctg | cgt | acc | 864 |
|---|---|---|---|---|---|---|---|---|---|---|---|---|---|---|---|---|
| Trp | Thr | Val | Leu | Ala | Ala | Pro | Leu | Leu | Met | Ser | Thr | Asp | Leu | Arg | Thr | |
| | | 275 | | | | | 280 | | | | | 285 | | | | |

| atc | tcc | gcc | cag | aac | atg | gac | att | ctg | cag | aat | cca | ctc | atg | atc | aaa | 912 |
|---|---|---|---|---|---|---|---|---|---|---|---|---|---|---|---|---|
| Ile | Ser | Ala | Gln | Asn | Met | Asp | Ile | Leu | Gln | Asn | Pro | Leu | Met | Ile | Lys | |
| | 290 | | | | | 295 | | | | | 300 | | | | | |

| atc | aac | cag | gat | ccc | tta | ggc | atc | cag | gga | cgc | agg | att | cac | aag | gaa | 960 |
|---|---|---|---|---|---|---|---|---|---|---|---|---|---|---|---|---|
| Ile | Asn | Gln | Asp | Pro | Leu | Gly | Ile | Gln | Gly | Arg | Arg | Ile | His | Lys | Glu | |
| 305 | | | | | 310 | | | | | 315 | | | | | 320 | |

| aaa | tct | ctc | atc | gaa | gtg | tac | atg | cgg | cct | ctg | tcc | aac | aag | gct | agc | 1008 |
|---|---|---|---|---|---|---|---|---|---|---|---|---|---|---|---|---|
| Lys | Ser | Leu | Ile | Glu | Val | Tyr | Met | Arg | Pro | Leu | Ser | Asn | Lys | Ala | Ser | |
| | | | | 325 | | | | | 330 | | | | | 335 | | |

| gcc | tta | gtc | ttc | ttc | agc | tgc | agg | acc | gat | atg | cct | tat | cgc | tac | cac | 1056 |
|---|---|---|---|---|---|---|---|---|---|---|---|---|---|---|---|---|
| Ala | Leu | Val | Phe | Phe | Ser | Cys | Arg | Thr | Asp | Met | Pro | Tyr | Arg | Tyr | His | |
| | | | 340 | | | | | 345 | | | | | 350 | | | |

```
tcc tcc ctt ggc cag ctg aac ttc acc ggg tct gtg ata tat gag gcc    1104
Ser Ser Leu Gly Gln Leu Asn Phe Thr Gly Ser Val Ile Tyr Glu Ala
        355                 360                 365 cag gac gtc tac tca ggt gac atc atc agt ggc ctc cga gat gaa acc    1152
Gln Asp Val Tyr Ser Gly Asp Ile Ile Ser Gly Leu Arg Asp Glu Thr
370                 375                 380 aac ttc aca gtg atc atc aac cct tca ggg gta gtg atg tgg tac ctg    1200
Asn Phe Thr Val Ile Ile Asn Pro Ser Gly Val Val Met Trp Tyr Leu
385                 390                 395                 400 tat ccc atc aag aac ctg gag atg tcc cag cag tga                     1236
Tyr Pro Ile Lys Asn Leu Glu Met Ser Gln Gln
                405                 410
```

<210> SEQ ID NO 4
<211> LENGTH: 411
<212> TYPE: PRT
<213> ORGANISM: Artificial Sequence
<220> FEATURE:
<223> OTHER INFORMATION: recombinant protein which is the amino-acid
      sequence of the mutant alpha-NAGA (alpha-NAGA S188E/A191L)

<400> SEQUENCE: 4

```
Met Leu Leu Lys Thr Val Leu Leu Gly His Val Ala Gln Val Leu
1               5                   10                  15

Met Leu Asp Asn Gly Leu Leu Gln Thr Pro Pro Met Gly Trp Leu Ala
                20                  25                  30

Trp Glu Arg Phe Arg Cys Asn Ile Asn Cys Asp Glu Asp Pro Lys Asn
            35                  40                  45

Cys Ile Ser Glu Gln Leu Phe Met Glu Met Ala Asp Arg Met Ala Gln
50                  55                  60

Asp Gly Trp Arg Asp Met Gly Tyr Thr Tyr Leu Asn Ile Asp Asp Cys
65                  70                  75                  80

Trp Ile Gly Gly Arg Asp Ala Ser Gly Arg Leu Met Pro Asp Pro Lys
                85                  90                  95

Arg Phe Pro His Gly Ile Pro Phe Leu Ala Asp Tyr Val His Ser Leu
            100                 105                 110

Gly Leu Lys Leu Gly Ile Tyr Ala Asp Met Gly Asn Phe Thr Cys Met
        115                 120                 125

Gly Tyr Pro Gly Thr Thr Leu Asp Lys Val Val Gln Asp Ala Gln Thr
    130                 135                 140

Phe Ala Glu Trp Lys Val Asp Met Leu Lys Leu Asp Gly Cys Phe Ser
145                 150                 155                 160

Thr Pro Glu Glu Arg Ala Gln Gly Tyr Pro Lys Met Ala Ala Ala Leu
                165                 170                 175

Asn Ala Thr Gly Arg Pro Ile Ala Phe Ser Cys Glu Trp Pro Leu Tyr
            180                 185                 190

Glu Gly Gly Leu Pro Pro Arg Val Asn Tyr Ser Leu Leu Ala Asp Ile
        195                 200                 205

Cys Asn Leu Trp Arg Asn Tyr Asp Asp Ile Gln Asp Ser Trp Trp Ser
    210                 215                 220

Val Leu Ser Ile Leu Asn Trp Phe Val Glu His Gln Asp Ile Leu Gln
225                 230                 235                 240

Pro Val Ala Gly Pro Gly His Trp Asn Asp Pro Asp Met Leu Leu Ile
                245                 250                 255

Gly Asn Phe Gly Leu Ser Leu Glu Gln Ser Arg Ala Gln Met Ala Leu
            260                 265                 270

Trp Thr Val Leu Ala Ala Pro Leu Leu Met Ser Thr Asp Leu Arg Thr
        275                 280                 285
```

```
Ile Ser Ala Gln Asn Met Asp Ile Leu Gln Asn Pro Leu Met Ile Lys
    290                 295                 300

Ile Asn Gln Asp Pro Leu Gly Ile Gln Gly Arg Arg Ile His Lys Glu
305                 310                 315                 320

Lys Ser Leu Ile Glu Val Tyr Met Arg Pro Leu Ser Asn Lys Ala Ser
                325                 330                 335

Ala Leu Val Phe Phe Ser Cys Arg Thr Asp Met Pro Tyr Arg Tyr His
            340                 345                 350

Ser Ser Leu Gly Gln Leu Asn Phe Thr Gly Ser Val Ile Tyr Glu Ala
        355                 360                 365

Gln Asp Val Tyr Ser Gly Asp Ile Ile Ser Gly Leu Arg Asp Glu Thr
    370                 375                 380

Asn Phe Thr Val Ile Ile Asn Pro Ser Gly Val Val Met Trp Tyr Leu
385                 390                 395                 400

Tyr Pro Ile Lys Asn Leu Glu Met Ser Gln Gln
                405                 410

<210> SEQ ID NO 5
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 5
gatgctgctg aagacagtgc tctt                                              24

<210> SEQ ID NO 6
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 6
tcactgctgg gacatctcca ggtt                                              24

<210> SEQ ID NO 7
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 7
aaaccgttgc tagcttaagt t                                                 21

<210> SEQ ID NO 8
<211> LENGTH: 35
<212> TYPE: DNA
<213> ORGANISM: Artificial Sequence
<220> FEATURE:
<223> OTHER INFORMATION: Chemically Synthesized

<400> SEQUENCE: 8
cccatcgcct tctcctgcga gtggccagcc tatga                                  35

<210> SEQ ID NO 9
<211> LENGTH: 28
<212> TYPE: DNA
<213> ORGANISM: Artificial Sequence
<220> FEATURE:
<223> OTHER INFORMATION: Chemically Synthesized
```

<400> SEQUENCE: 9
gcaggagaag gcgatggggc ggcctgtg                                28

<210> SEQ ID NO 10
<211> LENGTH: 35
<212> TYPE: DNA
<213> ORGANISM: Artificial Sequence
<220> FEATURE:
<223> OTHER INFORMATION: Chemically Synthesized

<400> SEQUENCE: 10
ttctcctgcg agtggccact ctatgaaggc ggcct                        35

<210> SEQ ID NO 11
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 11
tggccactcg caggagaagg cgatgggg                                28

<210> SEQ ID NO 12
<211> LENGTH: 1290
<212> TYPE: DNA
<213> ORGANISM: homo sapiens
<220> FEATURE:
<221> NAME/KEY: CDS
<222> LOCATION: (1)..(1290)

<400> SEQUENCE: 12

| atg | cag | ctg | agg | aac | cca | gaa | cta | cat | ctg | ggc | tgc | gcg | ctt | gcg | ctt | 48 |
| Met | Gln | Leu | Arg | Asn | Pro | Glu | Leu | His | Leu | Gly | Cys | Ala | Leu | Ala | Leu |
| 1 | | | | 5 | | | | | 10 | | | | | 15 | | |

| cgc | ttc | ctg | gcc | ctc | gtt | tcc | tgg | gac | atc | cct | ggg | gct | aga | gca | ctg | 96 |
| Arg | Phe | Leu | Ala | Leu | Val | Ser | Trp | Asp | Ile | Pro | Gly | Ala | Arg | Ala | Leu |
| | | | 20 | | | | | 25 | | | | | 30 | | | |

| gac | aat | gga | ttg | gca | agg | acg | cct | acc | atg | ggc | tgg | ctg | cac | tgg | gag | 144 |
| Asp | Asn | Gly | Leu | Ala | Arg | Thr | Pro | Thr | Met | Gly | Trp | Leu | His | Trp | Glu |
| | | 35 | | | | | 40 | | | | | 45 | | | | |

| cgc | ttc | atg | tgc | aac | ctt | gac | tgc | cag | gaa | gag | cca | gat | tcc | tgc | atc | 192 |
| Arg | Phe | Met | Cys | Asn | Leu | Asp | Cys | Gln | Glu | Glu | Pro | Asp | Ser | Cys | Ile |
| | 50 | | | | | 55 | | | | | 60 | | | | | |

| agt | gag | aag | ctc | ttc | atg | gag | atg | gca | gag | ctc | atg | gtc | tca | gaa | ggc | 240 |
| Ser | Glu | Lys | Leu | Phe | Met | Glu | Met | Ala | Glu | Leu | Met | Val | Ser | Glu | Gly |
| 65 | | | | 70 | | | | | 75 | | | | | 80 | | |

| tgg | aag | gat | gca | ggt | tat | gag | tac | ctc | tgc | att | gat | gac | tgt | tgg | atg | 288 |
| Trp | Lys | Asp | Ala | Gly | Tyr | Glu | Tyr | Leu | Cys | Ile | Asp | Asp | Cys | Trp | Met |
| | | | | 85 | | | | | 90 | | | | | 95 | | |

| gct | ccc | caa | aga | gat | tca | gaa | ggc | aga | ctt | cag | gca | gac | cct | cag | cgc | 336 |
| Ala | Pro | Gln | Arg | Asp | Ser | Glu | Gly | Arg | Leu | Gln | Ala | Asp | Pro | Gln | Arg |
| | | | 100 | | | | | 105 | | | | | 110 | | | |

| ttt | cct | cat | ggg | att | cgc | cag | cta | gct | aat | tat | gtt | cac | agc | aaa | gga | 384 |
| Phe | Pro | His | Gly | Ile | Arg | Gln | Leu | Ala | Asn | Tyr | Val | His | Ser | Lys | Gly |
| | | | 115 | | | | | 120 | | | | | 125 | | | |

| ctg | aag | cta | ggg | att | tat | gca | gat | gtt | gga | aat | aaa | acc | tgc | gca | ggc | 432 |
| Leu | Lys | Leu | Gly | Ile | Tyr | Ala | Asp | Val | Gly | Asn | Lys | Thr | Cys | Ala | Gly |
| | | 130 | | | | | 135 | | | | | 140 | | | | |

| ttc | cct | ggg | agt | ttt | gga | tac | tac | gac | att | gat | gcc | cag | acc | ttt | gct | 480 |
| Phe | Pro | Gly | Ser | Phe | Gly | Tyr | Tyr | Asp | Ile | Asp | Ala | Gln | Thr | Phe | Ala |
| 145 | | | | 150 | | | | | 155 | | | | | 160 | | |

-continued

| | |
|---|---|
| gac tgg gga gta gat ctg cta aaa ttt gat ggt tgt tac tgt gac agt<br>Asp Trp Gly Val Asp Leu Leu Lys Phe Asp Gly Cys Tyr Cys Asp Ser<br>165 170 175 | 528 |
| ttg gaa aat ttg gca gat ggt tat aag cac atg tcc ttg gcc ctg aat<br>Leu Glu Asn Leu Ala Asp Gly Tyr Lys His Met Ser Leu Ala Leu Asn<br>180 185 190 | 576 |
| agg act ggc aga agc att gtg tac tcc tgt gag tgg cct ctt tat atg<br>Arg Thr Gly Arg Ser Ile Val Tyr Ser Cys Glu Trp Pro Leu Tyr Met<br>195 200 205 | 624 |
| tgg ccc ttt caa aag ccc aat tat aca gaa atc cga cag tac tgc aat<br>Trp Pro Phe Gln Lys Pro Asn Tyr Thr Glu Ile Arg Gln Tyr Cys Asn<br>210 215 220 | 672 |
| cac tgg cga aat ttt gct gac att gat gat tcc tgg aaa agt ata aag<br>His Trp Arg Asn Phe Ala Asp Ile Asp Asp Ser Trp Lys Ser Ile Lys<br>225 230 235 240 | 720 |
| agt atc ttg gac tgg aca tct ttt aac cag gag aga att gtt gat gtt<br>Ser Ile Leu Asp Trp Thr Ser Phe Asn Gln Glu Arg Ile Val Asp Val<br>245 250 255 | 768 |
| gct gga cca ggg ggt tgg aat gac cca gat atg tta gtg att ggc aac<br>Ala Gly Pro Gly Gly Trp Asn Asp Pro Asp Met Leu Val Ile Gly Asn<br>260 265 270 | 816 |
| ttt ggc ctc agc tgg aat cag caa gta act cag atg gcc ctc tgg gct<br>Phe Gly Leu Ser Trp Asn Gln Gln Val Thr Gln Met Ala Leu Trp Ala<br>275 280 285 | 864 |
| atc atg gct gct cct tta ttc atg tct aat gac ctc cga cac atc agc<br>Ile Met Ala Ala Pro Leu Phe Met Ser Asn Asp Leu Arg His Ile Ser<br>290 295 300 | 912 |
| cct caa gcc aaa gct ctc ctt cag gat aag gac gta att gcc atc aat<br>Pro Gln Ala Lys Ala Leu Leu Gln Asp Lys Asp Val Ile Ala Ile Asn<br>305 310 315 320 | 960 |
| cag gac ccc ttg ggc aag caa ggg tac cag ctt aga cag gga gac aac<br>Gln Asp Pro Leu Gly Lys Gln Gly Tyr Gln Leu Arg Gln Gly Asp Asn<br>325 330 335 | 1008 |
| ttt gaa gtg tgg gaa cga cct ctc tca ggc tta gcc tgg gct gta gct<br>Phe Glu Val Trp Glu Arg Pro Leu Ser Gly Leu Ala Trp Ala Val Ala<br>340 345 350 | 1056 |
| atg ata aac cgg cag gag att ggt gga cct cgc tct tat acc atc gca<br>Met Ile Asn Arg Gln Glu Ile Gly Gly Pro Arg Ser Tyr Thr Ile Ala<br>355 360 365 | 1104 |
| gtt gct tcc ctg ggt aaa gga gtg gcc tgt aat cct gcc tgc ttc atc<br>Val Ala Ser Leu Gly Lys Gly Val Ala Cys Asn Pro Ala Cys Phe Ile<br>370 375 380 | 1152 |
| aca cag ctc ctc cct gtg aaa agg aag cta ggg ttc tat gaa tgg act<br>Thr Gln Leu Leu Pro Val Lys Arg Lys Leu Gly Phe Tyr Glu Trp Thr<br>385 390 395 400 | 1200 |
| tca agg tta aga agt cac ata aat ccc aca ggc act gtt ttg ctt cag<br>Ser Arg Leu Arg Ser His Ile Asn Pro Thr Gly Thr Val Leu Leu Gln<br>405 410 415 | 1248 |
| cta gaa aat aca atg cag atg tca tta aaa gac tta ctt taa<br>Leu Glu Asn Thr Met Gln Met Ser Leu Lys Asp Leu Leu<br>420 425 | 1290 |

<210> SEQ ID NO 13
<211> LENGTH: 429
<212> TYPE: PRT
<213> ORGANISM: homo sapiens

<400> SEQUENCE: 13

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu

```
                  20                  25                  30
Asp Asn Gly Leu Ala Arg Thr Pro Thr Met Gly Trp Leu His Trp Glu
            35                  40                  45

Arg Phe Met Cys Asn Leu Asp Cys Gln Glu Pro Asp Ser Cys Ile
50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
            85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
            115                 120                 125

Leu Lys Leu Gly Ile Tyr Ala Asp Val Gly Asn Lys Thr Cys Ala Gly
            130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
            195                 200                 205

Trp Pro Phe Gln Lys Pro Asn Tyr Thr Glu Ile Arg Gln Tyr Cys Asn
210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
            275                 280                 285

Ile Met Ala Ala Pro Leu Phe Met Ser Asn Asp Leu Arg His Ile Ser
290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
            355                 360                 365

Val Ala Ser Leu Gly Lys Gly Val Ala Cys Asn Pro Ala Cys Phe Ile
            370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425

<210> SEQ ID NO 14
<211> LENGTH: 45
```

```
<212> TYPE: DNA
<213> ORGANISM: homo sapiens
<220> FEATURE:
<221> NAME/KEY: CDS
<222> LOCATION: (1)..(45)

<400> SEQUENCE: 14 atg tct gca ctt ctg atc cta gct ctt gtt gga gct gca gtt gct         45
Met Ser Ala Leu Leu Ile Leu Ala Leu Val Gly Ala Ala Val Ala
1               5                  10                  15

<210> SEQ ID NO 15
<211> LENGTH: 15
<212> TYPE: PRT
<213> ORGANISM: homo sapiens

<400> SEQUENCE: 15

Met Ser Ala Leu Leu Ile Leu Ala Leu Val Gly Ala Ala Val Ala
1               5                  10                  15
```

HIGHLY FUNCTIONAL ENZYME HAVING α-GALACTOSIDASE ACTIVITY

CROSS-REFERENCE TO RELATED APPLICATIONS

This application is a Divisional of U.S. application Ser. No. 13/052,632, filed on Mar. 21, 2011, now U.S. Pat. No. 8,323,640, which is a Divisional of U.S. application Ser. No. 12/084,982, filed on May 14, 2008, now U.S. Pat. No. 7,935,336, which is a U.S. National Stage of International Application PCT/JP2006/323509, filed on Nov. 17, 2006 and claiming priority to Japanese Application No. 2005-333660, filed on Nov. 18, 2005, the entirety of which is incorporated herein by reference.

TECHNICAL FIELD

The present invention relates to a recombinant protein having α-galactosidase activity.

BACKGROUND ART

For hereditary enzyme deficiency, for which no radical treatments have been known to date, enzyme replacement therapy in which an enzyme is produced by genetic engineering and is then administered in a blood vessel by intravenous drip or the like has been developing. As an example of hereditary enzyme deficiency whose prevalence is relatively high and which is designated as a specified disease (intractable disease), Fabry disease (hereditary α-galactosidase deficiency, which is one of a group of genetic diseases and also called lysosomal disease), is well known (refer to Kenneth J. Dean et al., Fabry Disease, "Practical Enzymology of the Sphingolipidoses", U.S.A., Aln R. Liss, Inc., 1997, p. 173-216).

Fabry disease is a glycolipid metabolic disorder which develops as follows: As a result of a decrease in the activity of an enzyme called "α-galactosidase", which is one of the enzymes present in a lysosome, which is one of the human intracellular organelles, and deficiency of the enzyme, a glycolipid called globotriaosylceramide (also referred to as ceramide trihexoside), which is an in vivo substrate of the enzyme, is not decomposed and accumulated in the body (for example, blood vessels, skins, cornea, nerves, kidneys, and heart).

Since a gene encoding α-galactosidase lies on the X chromosome, this disease has a mode of X-chromosomal inheritance. Therefore, in this disease, a definite clinical feature is observed mainly in hemizygote in males. It is believed that "classic Fabry disease", which takes a typical clinical course, develops in about one out of 40,000 male children. Symptoms such as pain in the hand and the foot, hypohidrosis, angiokeratoma, and corneal opacity appear during the juvenile term and adolescence; these symptoms progress and then cause systemic organ damage such as renal failure, heart failure, and cerebrovascular disorder during middlescence and thereafter; and these become the cause of death. In addition, a disease which does not take such a typical clinical course as "classic Fabry disease" and which develops late and takes a relatively moderate course, is "variant Fabry disease". In patients having this type of disease, residual α-galactosidase activity is observed though it is low. As a variant Fabry disease, for example, "cardiac Fabry disease" is known. The above-mentioned glycolipid accumulation mainly occurs in the heart. Thereby, cardiac hypertrophy occurs, and disorders such as heart failure and arrhythmia are caused. On the other hand, in female heterozygote Fabry patients, various types of clinical features are observed in accordance with the characteristics of the X chromosome. Specifically, cases ranging from serious cases which are similar to those of hemizygote in males to cases in which substantially no symptoms are observed exist. However, according to recent research, it has become clear that most female heterozygote Fabry patients develop some symptoms when they become old. There is a viewpoint that they should be treated not as "carriers" but as "patients".

Recently, enzyme replacement therapy for Fabry disease has also been established, and a recombinant human α-galactosidase produced in a cell derived from mammals has been widely used as an active ingredient of a Fabry disease therapeutic agent in the above therapy (refer to Eng C M et al., Am J Hum Genet, 68: 711-722 (2001); Eng C M et al., N Engl J Med, 345: 9-16 (2001); and Schiffmann R et al., Proc Natl Acad Sci USA, 97: 365-370 (2000)).

Furthermore, a method in which a recombinant human α-galactosidase produced using a cell (for example, yeast) other than an animal cell as a host is used for the medical treatment (enzyme replacement therapy) of Fabry disease (refer to Japanese Unexamined Patent Application Publication No. 2002-369692), a gene therapeutic method in which an enzyme is replaced by introducing a gene encoding human α-galactosidase into a cell of an affected tissue to express the gene (refer to Japanese Unexamined Patent Application Publication (Translation of PCT Application) No. 2002-522509), and the like have also been proposed.

DISCLOSURE OF INVENTION

However, since an existing enzyme agent used in enzyme replacement for treating Fabry disease is often administered to patients who originally do not have an enzyme (human α-galactosidase), the enzyme contained in the therapeutic agent is recognized as a foreign substance in many patients administered with the enzyme agent, and thus, an antibody is produced. As a result, adverse side effects, mainly, allergic reactions are expressed at a high frequency. This similarly occurs in the case where the enzyme is replaced using a method of gene therapy.

In addition, such an enzyme agent used in enzyme replacement is administered in blood vessels, but α-galactosidase itself is unstable in blood. Accordingly, in the actual therapy, the enzyme agent must be frequently administered (once every two weeks), and it may be necessary to increase the dosage per administration. Furthermore, human α-galactosidase has a relatively small number of sugar chains (N-type sugar chains) to which mannose-6-phosphate (M6P) residue can be bonded, the sugar chains being necessary for human α-galactosidase to be incorporated into a cell (more specifically, into a lysosome in a cell) in an affected organ. Therefore, it is difficult for human α-galactosidase to be taken from blood and incorporated into a cell. In particular, the incorporation efficiency in the kidney or heart, which is the main affected organ in Fabry disease, is low, and thus the therapeutic effect for nephropathy or cardiopathy is insufficient. Accordingly, in order to allow a certain amount of enzyme to be incorporated into a target cell in therapy, a large amount of enzyme is required. Consequently, it is necessary to administer an enzyme agent used in enzyme replacement more frequently and in a larger amount. Such therapy places a large burden on patients physically, mentally, and economically, and thus adversely affects the "quality of life (QOL)".

Accordingly, it is an object of the present invention to provide, as an enzyme which can be used for enzyme replacement therapy for Fabry disease, a protein having α-galactosidase activity, which shows no allergic adverse side effect, shows a high stability in blood (in plasma), and can be easily incorporated into a cell of an affected organ.

The present inventors conducted intensive studies in order to solve the above problems. As a result, the present inventors focused on "α-N-acetylgalactosaminidase (α-NAGA)", which has a substrate specificity different from that of α-galactosidase but which has a three-dimensional structure very similar to that of α-galactosidase as a whole. The present inventors have found that when the substrate specificity of α-NAGA is converted so as to have α-galactosidase activity by changing the structure of the active site of α-NAGA using a gene recombination technique, an excellent novel highly functional enzyme for treating Fabry disease that can be used to solve the above problems can be created. This finding resulted in completion of the present invention.

More specifically, the present invention is as follows:

(1) A protein which has acquired α-galactosidase activity by changing the structure of the active site of wild-type human α-N-acetylgalactosaminidase.

An example of the protein is a protein having the substrate specificity of α-galactosidase.

(2) A protein having α-galactosidase activity, the protein being composed of an amino-acid sequence in which at least one of the 188th amino acid and the 191st amino acid in the amino-acid sequence of wild-type human α-N-acetylgalactosaminidase is replaced with another amino acid, or an amino-acid sequence in which one or several amino acids except the 188th amino acid and the 191st amino acid included in the replaced amino-acid sequence are deleted, replaced, or added.

An example of the protein is a protein wherein the 188th amino acid is replaced with glutamic acid or aspartic acid in the replacement with another amino acid.

In addition, another example of the protein is a protein wherein the 191st amino acid is replaced with one selected from the group consisting of leucine, valine, isoleucine, phenylalanine, and methionine in the replacement with another amino acid.

Furthermore, another example of the protein is a protein wherein the 188th amino acid is replaced with glutamic acid, and the 191st amino acid is replaced with leucine in the replacement with another amino acid.

(3) A protein described by (a) or (b):
   (a) a protein containing any one of amino-acid sequences described by (i) to (iii):
      (i) an amino-acid sequence composed of the 18th amino acid to the 411th amino acid included in an amino-acid sequence in which the 188th amino acid is replaced with an amino acid other than serine in the amino-acid sequence shown in sequence No. 2;
      (ii) an amino-acid sequence composed of the 18th amino acid to the 411th amino acid included in an amino-acid sequence in which the 191st amino acid is replaced with an amino acid other than alanine in the amino-acid sequence shown in sequence No. 2; and
      (iii) an amino-acid sequence composed of the 18th amino acid to the 411th amino acid included in an amino-acid sequence in which the 188th amino acid is replaced with an amino acid other than serine and the 191st amino acid is replaced with an amino acid other than alanine in the amino-acid sequence shown in sequence No. 2; or
   (b) a protein containing an amino-acid sequence in which one or several amino acids other than the amino acid or amino acids located at the replacement site or sites are deleted, replaced, or added in any one of amino-acid sequences described by (i) to (iii), and having α-galactosidase activity.

An example of the protein is a protein wherein the amino acid other than serine is glutamic acid or aspartic acid.

In addition, another example of the protein is a protein wherein the amino acid other than alanine is one selected from the group consisting of leucine, valine, isoleucine, phenylalanine, and methionine.

Furthermore, another example of the protein is a protein wherein the amino acid other than serine is glutamic acid, and the amino acid other than alanine is leucine.

(4) A gene encoding the protein according to any one of items (1) to (3).

(5) A gene containing DNA described by (a) or (b):
   (a) DNA containing any one of base sequences described by (i) to (iii):
      (i) a base sequence composed of the 52nd to 1,236th bases included in a base sequence in which the 562nd to 564th bases are replaced with bases representing a codon of an amino acid other than serine in the base sequence shown in sequence No. 1;
      (ii) a base sequence composed of the 52nd to 1,236th bases included in a base sequence in which the 571st to 573rd bases are replaced with bases representing a codon of an amino acid other than alanine in the base sequence shown in sequence No. 1; and
      (iii) a base sequence composed of the 52nd to 1,236th bases included in a base sequence in which the 562nd to 564th bases are replaced with bases representing a codon of an amino acid other than serine and the 571st to 573rd bases are replaced with bases representing a codon of an amino acid other than alanine in the base sequence shown in sequence No. 1; or
   (b) DNA which encodes a protein having α-galactosidase activity and which hybridizes with DNA composed of a base sequence complementary to DNA containing any one of base sequences described by (i) to (iii) under a stringent condition, wherein bases corresponding to the bases at the replacement sites are identical to the bases at the replacement sites.

An example of the gene is a gene wherein the amino acid other than serine is glutamic acid or aspartic acid.

In addition, another example of the gene is a gene wherein the amino acid other than alanine is one selected from the group consisting of leucine, valine, isoleucine, phenylalanine, and methionine.

Furthermore, another example of the gene is a gene wherein the amino acid other than serine is glutamic acid, and the amino acid other than alanine is leucine.

(6) A recombinant vector containing the gene according to item (4) or (5).

(7) A transformant containing the recombinant vector according to item (6).

(8) A method of producing a protein having α-galactosidase activity, wherein the structure of the active site of wild-type human α-N-acetylgalactosaminidase is changed so that a substrate of α-galactosidase can be bound to the active site.

(9) A method of producing a protein having α-galactosidase activity including a step of culturing the transformant according to item (7), and a step of collecting the protein having α-galactosidase activity from the resulting cultured product.

(10) A pharmaceutical composition containing the protein according to any one of items (1) to (3).

(11) A therapeutic agent for Fabry disease containing the pharmaceutical composition according to item (10) as an active ingredient.

(12) A pharmaceutical composition containing the gene according to item (4) or (5).

(13) A gene therapeutic agent for Fabry disease containing the pharmaceutical composition according to item (12) as an active ingredient.

(14) A method of treating Fabry disease, wherein the pharmaceutical composition according to item (10) or (12) is administered to a Fabry patient.

BEST MODES FOR CARRYING OUT THE INVENTION

Figure 1:
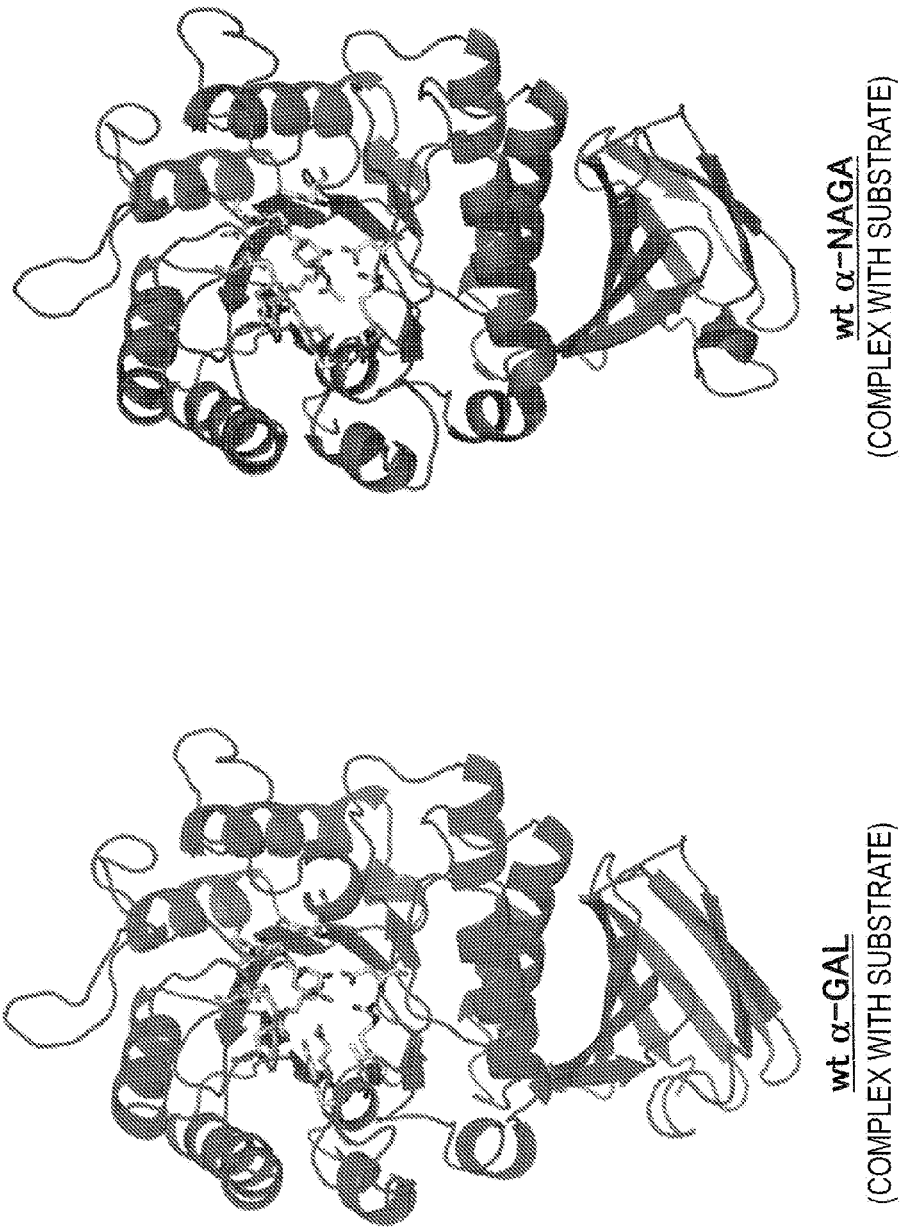
FIG. 1 includes schematic views showing the three-dimensional overall structures of a subunit of wild-type α-GAL and a subunit of wild-type α-NAGA.

The present invention will now be described in detail, but the scope of the present invention is not restricted by the descriptions below. In addition to exemplifications described below, various modifications can be made to the present invention without departing from the purpose of the present invention.

This description includes the entirety of the specification of Japanese Patent Application No. 2005-333660, which claims the priority of this application. In addition, all publications, for example, prior art documents, unexamined patent application publications, patent publications, and other patent documents cited in this description are incorporated in this description as references.

1. Summary of the Present Invention

The present invention provides a recombinant protein serving as an excellent novel highly functional enzyme which can be used for enzyme replacement therapy for Fabry disease.

For existing enzyme agents used in enzyme replacement for treating Fabry disease, recombinant human α-galactosidase produced in a cell derived from mammals, such as a (Chinese hamster ovary) CHO cell or a human fibroblast, is used. However, the use of the recombinant human α-galactosidase causes problems such as allergic adverse side effects, instability in blood, and low incorporation efficiency into a cell of an affected organ, and thus places a very large burden on patients in the actual therapy. Accordingly, a solution to these problems has been desired.

In order to solve these problems, the present inventors studied whether or not an enzyme other than α-galactosidase (α-GAL) can be used as an enzyme used in enzyme replacement for treating Fabry disease. Specifically, the present inventors focused on "α-N-acetylgalactosaminidase (α-NAGA)", which is a lysosomal enzyme similarly to α-GAL (that is, the localization of α-NAGA in a cell being the same as that of α-GAL), which has a substrate specificity different from that of α-GAL, but which has a three-dimensional structure very similar to that of α-GAL as a whole.

α-GAL used to be called α-galactosidase A. It was believed that an isozyme called α-galactosidase B having biochemical properties which are very similar to those of α-GAL existed. It was known that α-galactosidase B had higher stability than that of α-GAL, but did not have the ability to decompose globotriaosylceramide, which is accumulated in the body by Fabry disease. Afterward, it became clear that α-galactosidase B is actually α-N-acetylgalactosaminidase (α-NAGA). It is known that α-NAGA is encoded by a gene which is considered to be derived from the same ancestor gene as that of a gene encoding α-GAL. The cDNA thereof has been cloned, and it is known that the gene encodes a protein composed of 411 amino acid residues containing a signal peptide composed of 17 amino acid residues. In addition, when the structure of human α-NAGA is compared with that of human α-GAL, the structure of human α-NAGA has the homology of 57.9% in terms of the base sequence level, and 52.2% in terms of the amino-acid sequence level. Furthermore, as in human α-GAL, human α-NAGA is an enzyme that exists in the form of a homodimer.

On the basis of the above knowledge, the present inventors first constructed three-dimensional structural models of α-NAGA and α-GAL, and compared the structures. More specifically, a three-dimensional structural model of human α-NAGA was constructed with reference to the structural information of chicken α-NAGA (ID: 1KTC) registered in Protein Data Bank (PDB www.rcsb.org/pdb/)), and this structure was compared with the three-dimensional structure of human α-GAL (ID: 1R47) registered in PDB. As a result, it was found that the three-dimensional structure of human α-NAGA was very similar to the three-dimensional structure of human α-GAL in terms of both the entire structure and the active site. Regarding the active site, to be exact, only a few amino acid residues are different from each other. However, among these amino acid residues, there are important amino acid residues which are present in a substrate-binding site and which affect the difference between the substrate specificity of α-GAL and the substrate specificity of α-NAGA. It was found that, in this regard, there is a significant difference in the three-dimensional structure between the active site of α-GAL and the active site of α-NAGA.

Figure 2A:
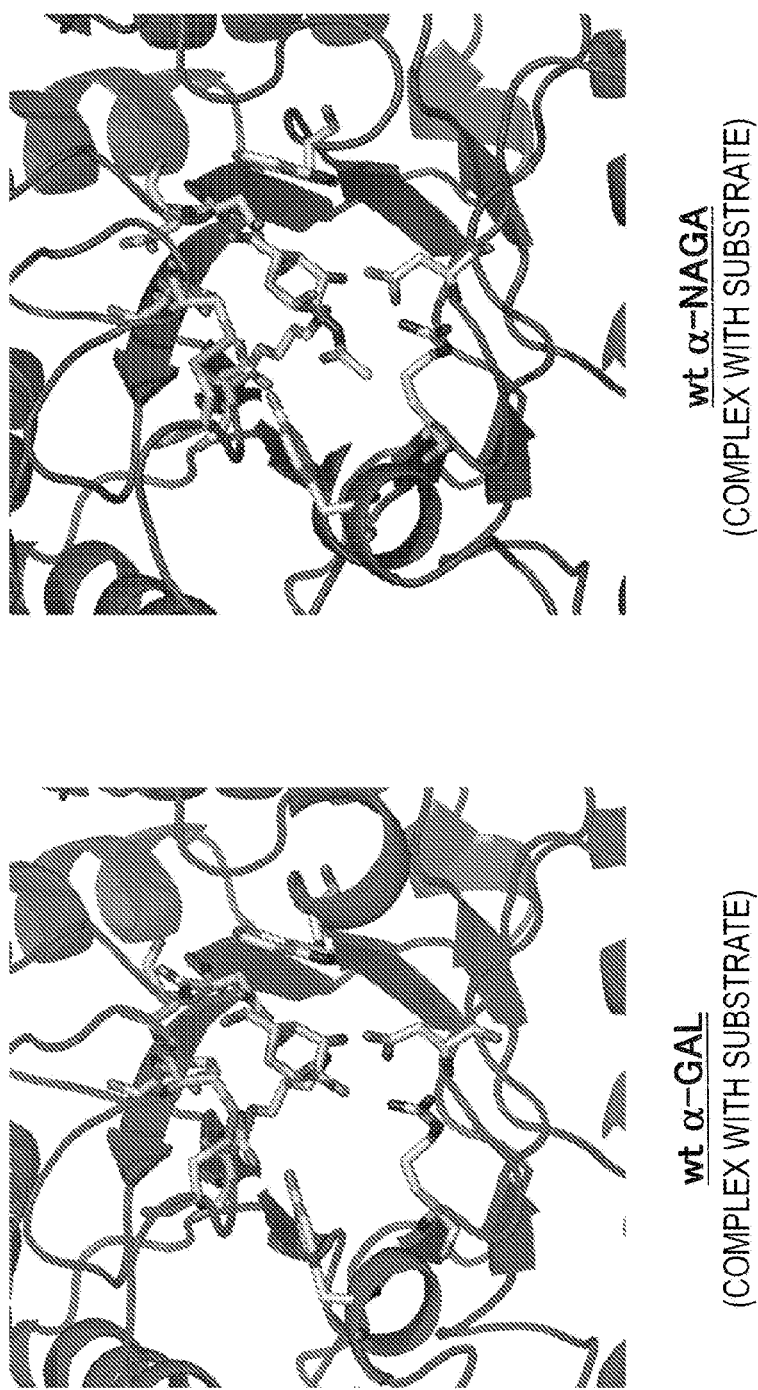
FIG. 2A includes schematic views showing the structures of the active site of wild-type α-GAL and the active site of wild-type α-NAGA. Note that the amino acids (shown by a stick model (except a substrate)) shown in the figure are the same type of amino acids in the case where the amino-acid sequence of the active site of wild-type α-GAL is compared with that of wild-type α-NAGA.
Figure 2B:
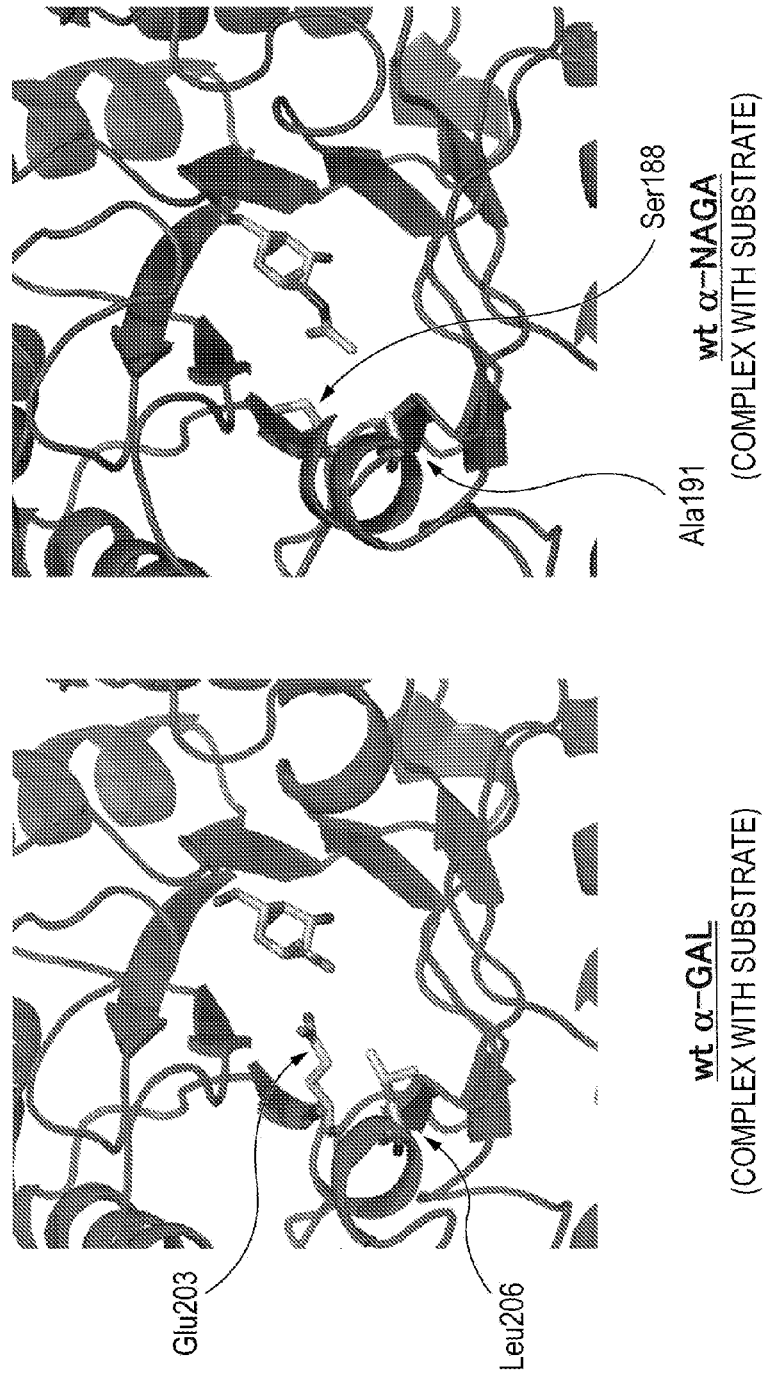
FIG. 2B includes schematic views showing the structures of the active site of wild-type α-GAL and the active site of wild-type α-NAGA. Note that the amino acids (shown by a stick model (except a substrate)) shown in the figure are different types of amino acids in the case where the amino-acid sequence of the active site of wild-type α-GAL is compared with that of wild-type α-NAGA.

Thus, α-NAGA is an enzyme which differs from α-GAL in the structure of a part of the substrate-binding site in the active site but is very similar to α-GAL in terms of the structure and in terms of properties regarding the other parts including the catalytic site (refer to FIGS. 1, 2A, and 2B). Therefore, the catalytic reaction mechanism of α-NAGA is very similar to the catalytic reaction mechanism of α-GAL in terms of, for example, the types of reaction substrate used and reaction product produced.

Consequently, as described above, the present inventors focused on α-NAGA and found that when the substrate specificity of α-NAGA is modified so as to have α-galactosidase activity by changing the structure of the active site (in particular, the substrate-binding site) by gene manipulation of α-NAGA (for example, when, among amino acid residues related to the substrate recognition of α-NAGA, key amino acid residues are changed from α-NAGA-type amino acid residues to α-GAL-type amino acid residues), a novel excellent highly functional enzyme for treating Fabry disease can be created.

The reasons why the present inventors focused on α-NAGA further include the following points (i) to (iii):

(i) α-NAGA is the responsible enzyme of Shindler disease and Kanzaki disease (note that a disease that develops due to abnormality of the same enzyme as an enzyme that develops Shindler disease and that has a clinical phenotype different from that of Shindler disease is called Kanzaki disease), and deficiency of α-NAGA is a cause of the development of Shindler disease and Kanzaki disease. In general, however, the development of Shindler disease and Kanzaki disease is very rare even in Fabry patients. Accordingly, almost all Fabry patients have α-NAGA normally. Therefore, it is believed that even when a protein in which only the substrate specificity of α-NAGA is modified into the substrate specificity of α-GAL is administered as an enzyme agent used in enzyme replacement, the antigenicity thereof rarely appears as in the case where wild-type α-NAGA is administered, and thus there is substantially no probability that an adverse immune reaction such as an allergic side effect is induced.

(ii) α-NAGA also functions in the form of a homodimer similarly to α-GAL, but in general, the stability in the dimer form of α-NAGA is higher than that of α-GAL. The three-dimensional structural model constructed by the present inventors also supports this stability. Specifically, it was confirmed that, in the dimer of human α-NAGA, two bonds due to electrostatic interaction were observed between Asp45 and Arg350 in two subunits, whereas such bonds were not observed in α-GAL. Accordingly, it is believed that, as in α-NAGA, an α-NAGA mutant also has high stability in blood (in plasma), compared with α-GAL, and is very suitable for enzyme replacement therapy. In addition, if the existing dimer proportion is increased because of the above stability, it is expected that the incorporation efficiency into a lysosome in a cell is also improved in relation to point (iii) below. Furthermore, it is advantageous in that, before administration, the effect can be maintained as an enzyme preparation for a long period.

Figure 3:
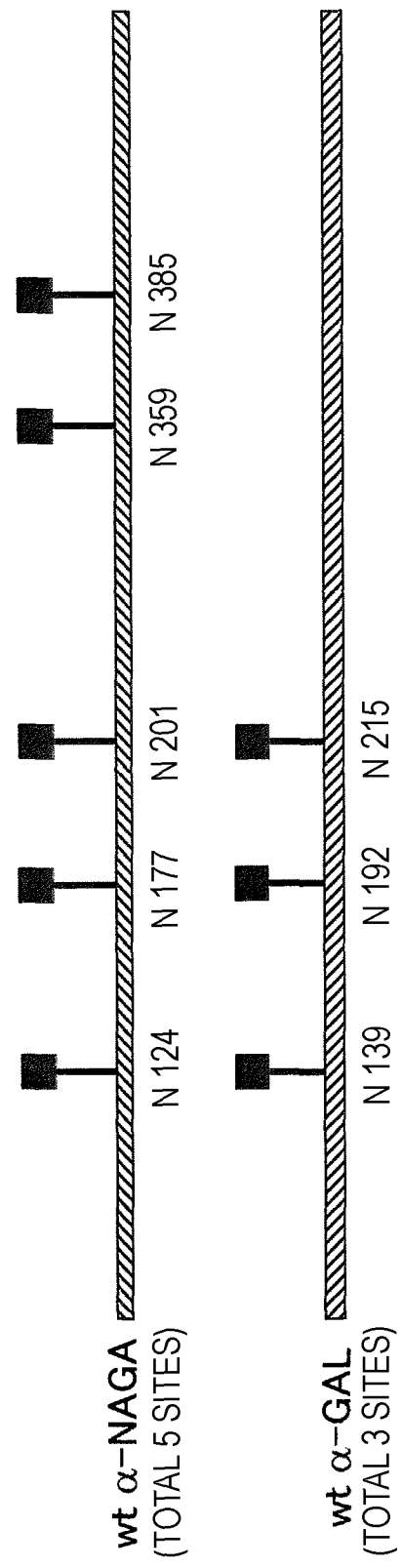
FIG. 3 includes schematic views showing the comparison between the number of N-glycosylation sites and locations thereof in the subunit of wild-type α-GAL and those in the subunit of wild-type α-NAGA.
Figure 4:
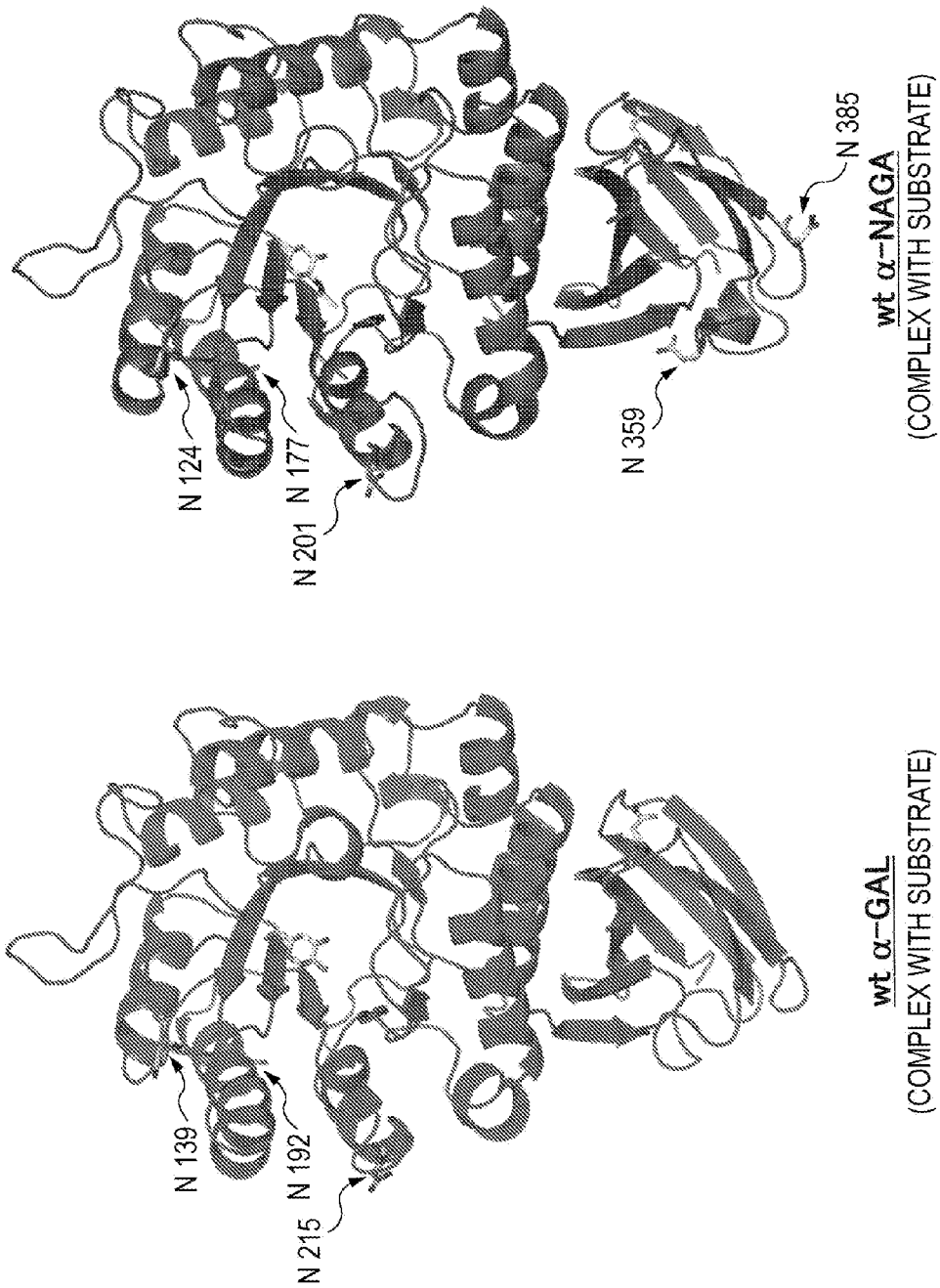
FIG. 4 includes schematic views in which the N-glycosylation sites (shown by a stick model (except a substrate)) in the subunits of wild-type α-GAL and wild-type α-NAGA are shown in the three-dimensional structures of the subunits.

(iii) It is necessary that an enzyme used in enzyme replacement therapy be incorporated into a lysosome in a cell of an affected organ. In general, the transportation from a cell membrane to a lysosome is performed via a calcium-independent M6P receptor, which recognizes mannose-6-phosphate (M6P) present in sugar chain portions of the enzyme. Accordingly, an enzyme having a large number of sugar chains (N-type sugar chains) to which the residue of M6P residue can be bonded is preferable because a high incorporation efficiency into a lysosome can be achieved. Regarding the number of the above sugar chains, it has become clear that, from X-ray crystal structure analysis, in α-GAL, three sugar chains per subunit (three locations of Asn139, Asn192, and Asn215; six sugar chains in the case where a dimer is formed) are present. In contrast, in α-NAGA, five sugar chains per subunit (ten sugar chains in the case where a dimer is formed) are present (refer to FIGS. 3 and 4). Among these sugar chains, three sugar chains (three locations of Asn124, Asn177, and Asn201) correspond to the locations of the sugar chains in α-GAL, and two other sugar chains (two locations of Asn359 and Asn385) are specific to α-NAGA. Accordingly, it is believed that α-NAGA is taken from blood and incorporated into a lysosome in a cell of an affected organ at a higher efficiency than that in the case of α-GAL.

From the above standpoints, the present inventors focused on the 188th amino acid (serine (Ser)) and the 191st amino acid (Ala (alanine)) among an amino-acid residue group constituting the substrate-binding site of α-NAGA. The present inventors prepared a recombinant enzyme (mutant enzyme) in which the 188th serine (Ser) is replaced with glutamic acid (Glu) and the 191st alanine is replaced with leucine (Leu) (refer to Examples 1 and 2). Subsequently, this recombinant enzyme was expressed using a fibroblast derived from a Fabry patient, collected, and analyzed. As a result, high α-GAL activity was observed (refer to Example 2). In addition, the stability of this recombinant enzyme in blood was significantly higher than that of wild-type α-GAL (refer to Example 3 and FIG. 5). By using such a recombinant enzyme having a modified substrate specificity, an enzyme agent used in enzyme replacement for treating Fabry Disease which is superior to existing enzyme agents can be provided.

Note that, in this description, unless otherwise stated, the terms "α-galactosidase" and "α-GAL" mean "human α-galactosidase A, and the terms "α-N-acetylgalactosaminidase" and "α-NAGA" mean "human α-N-acetylgalactosaminidase". The orders "the 188th" and "the 191st" represent locations based on the amino-acid sequence of α-NAGA shown in sequence No. 2.

2. Protein

A protein of the present invention is a mutant enzyme of α-N-acetylgalactosaminidase (α-NAGA). More specifically, the protein of the present invention is a protein which has acquired α-galactosidase (α-GAL) activity by changing the structure of the active site (in particular, the substrate-binding site) of wild-type α-NAGA, and preferably, a protein having the substrate specificity of α-GAL.

Herein, the phrase "has acquired α-GAL activity" means that, in the substrate-binding site of α-NAGA, the binding reactivity to a substrate of α-GAL becomes relatively higher than the binding reactivity to a substrate of α-NAGA. Accordingly, the above structural change is not limited to a structural change which makes it impossible for α-NAGA to bind with the substrate of α-NAGA. Alternatively, the structural change may be a structural change that makes the binding reactivity to the substrate of α-GAL significantly higher than the binding reactivity to the substrate of α-NAGA, which has originally been relatively significantly higher than the binding reactivity to the substrate of α-GAL. Furthermore, the phrase "having the substrate specificity of α-GAL" means that the structure (in particular, the positions and the types of amino acid residues which play an important role in the binding reactivity to a substrate) of the active site of the protein is the same as that of α-GAL.

In the present invention, the term "substrate of α-GAL" means a natural compound such as a glycolipid, e.g., globotriaosylceramide, which has a galactose residue bound to the non-reducing end by α-bonding, or a synthetic compound, e.g., 4-methylumbelliferyl-α-D-galactoside. The term "substrate of α-NAGA" means a natural compound such as an oligosaccharide, glycoprotein, or glycolipid having an N-acetylgalactosamine residue bound to the non-reducing end by α-bonding, or a synthetic compound, e.g., 4-methylumbelliferyl-α-N-acetyl-D-galactosaminide.

Here, a catalytic reaction of wild-type α-GAL is shown by reaction formula (1), and a catalytic reaction of wild-type α-NAGA is shown by reaction formula (2).

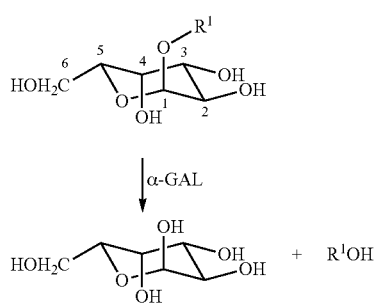

[In formula (1), when the substrate is a natural compound, R¹ represents "a group derived from a sugar complex", and when the substrate is a synthetic compound, R¹ represents "a 4-methylumbelliferyl group".]

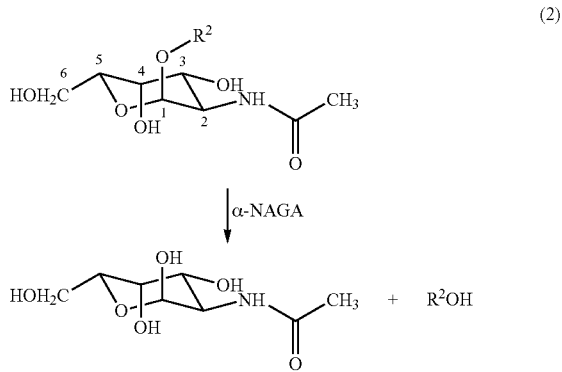

[In formula (2), when the substrate is a natural compound, R² represents "a group derived from a sugar complex", and when the substrate is a synthetic compound, R² represents "a 4-methylumbelliferyl group".]

Examples of the protein of the present invention preferably include proteins which are composed of an amino-acid sequence in which at least one of the 188th amino acid and the 191st amino acid included in the amino-acid sequence of wild-type α-NAGA is replaced with another amino acid (more preferably, an amino-acid sequence in which both the 188th amino acid and the 191st amino acid are replaced with other amino acids) or an amino-acid sequence in which one or several amino acids except the 188th amino acid and the 191st amino acid included in the above replaced amino-acid sequence are deleted, replaced, or added and which have α-GAL activity. Information on the amino-acid sequence (sequence No. 2) of the subunit of wild-type α-NAGA (homodimer) and information on the base sequence (sequence No. 1) encoding the above amino-acid sequence are published, for example, as "accession number: NM_000262" in GenBank, and registered as "entry name: NAGAB_HUMAN", accession number: P17050" in Swiss-Prot (available from tw.expasy.org/uniprot/). Similarly, information on the amino-acid sequence (sequence No. 13) of the subunit of wild-type α-GAL (homodimer) and information on the base sequence (sequence No. 12) encoding the above amino-acid sequence are published, for example, as "accession number: NP_000160" in GenBank, and registered as "entry name: AGAL_HUMAN", accession number: P06280" in Swiss-Prot (available from tw.expasy.org/uniprot/).

Herein, examples of the above "amino-acid sequence in which one or several amino acids are deleted, replaced, or added" preferably include amino-acid sequences in which about one to ten amino acids, and preferably about one to five amino acids are deleted, replaced, or added.

Furthermore, regarding the protein composed of an amino-acid sequence in which one or several amino acids are deleted, replaced, or added", it is important that the protein can stably exhibit α-GAL activity. Therefore, for example, all of or some of (preferably, all of) the 28th to 31st amino acids, the 77th to 81st amino acids, the 117th to 127th amino acids, the 150th to 158th amino acids, the 192nd amino acid, the 209th to 220th amino acids, and the 242nd to 254th amino acids (in particular, the 156th and 217th aspartic acids (Asp: D)), all of which are believed to be important for the binding performance (substrate-binding performance) with an α-galactose residue in a substrate of α-GAL and the catalytic reactivity to the substrate; the 45th aspartic acid (Asp: D) and the 350th arginine (Arg: R), both of which are believed to be important for forming a homodimer; and the 124th, 177th, 201st, 359th, and 385th amino acids (all of which being asparagine (Asn: N)), all of which are N-type-sugar-chain-binding sites, are preferably amino acids which are not mutated (deleted, replaced, or added) from the amino-acid sequence of wild-type α-NAGA.

Regarding the 188th amino acid residue, the other alternative amino acid residue is not particularly limited as long as the amino acid residue is not serine (Ser: S). For example, glutamic acid (Glu: E) and aspartic acid (Asp: D) are preferable, and glutamic acid is more preferable. Similarly, regarding the 191st amino acid residue, the other alternative amino acid residue is not particularly limited as long as the amino acid residue is not alanine (Ala: A). For example, leucine (Leu: L), valine (Val: V), isoleucine (Ile: I), phenylalanine (Phe: F), and methionine (Met: M) are preferable, and leucine is more preferable. Particularly preferably, among these, as the alternative amino acids, the 188th amino acid is glutamic acid and the 191st amino acid is leucine. Note that, preferably, the amino acids after the replacement do not substantially affect the structure composed of other amino acids which are not replaced. From this point of view, in a particularly preferable replacement embodiment, the 188th amino acid residue is glutamic acid and the 191st amino acid residue is leucine.

Figure 6:
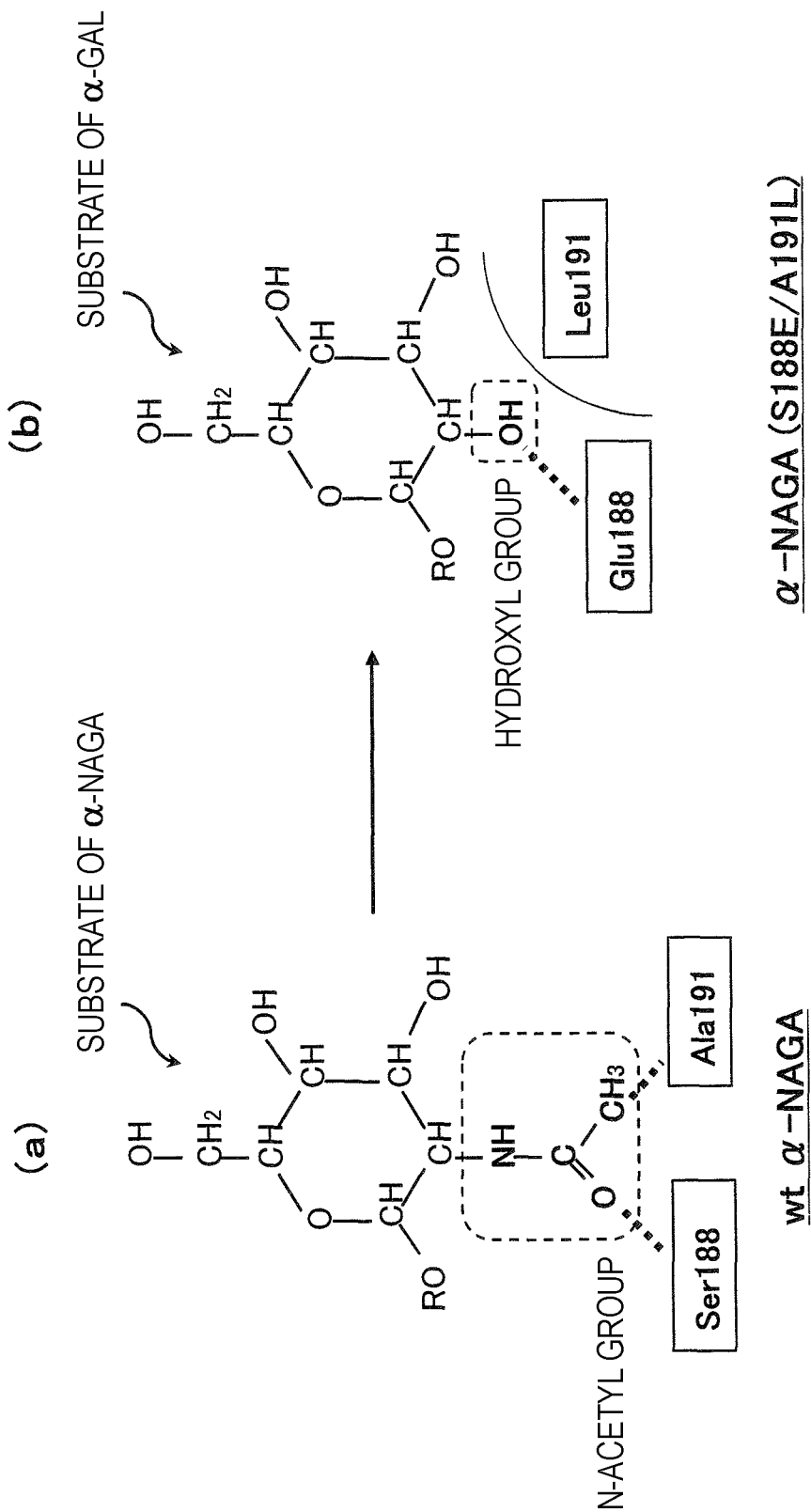
FIG. 6(a) is a schematic view showing a state in which wild-type α-NAGA is bonded to a substrate of α-NAGA.
FIG. 6(b) is a schematic view showing a state in which α-NAGA(S188E/A191L), which is an α-NAGA mutant, is bonded to a substrate of α-GAL.

By replacing the 188th amino acid and the 191st amino acid, both of which are present in the substrate-binding site, as described above, the following effects can be achieved. Specifically, as exemplified in FIG. 6, regarding the 188th amino acid residue, the interaction with the N-acetyl group (in particular, the oxygen atom) in the substrate of α-NAGA can be removed, and in addition, a binding action with the hydroxyl group in the substrate of α-GAL can be generated. Regarding the 191st amino acid residue, the interaction with the N-acetyl group (in particular, the methyl group) in the substrate of α-NAGA can be removed, and in addition, the binding space of the substrate (in particular, the space into which the N-acetyl group is taken) can be restricted. As a result, the recombinant enzyme (recombinant protein) obtained after the replacement of amino acids has a binding reactivity to the substrate of α-GAL higher than the binding reactivity to the substrate of α-NAGA, and thus can be an enzyme having α-GAL activity significantly higher than α-NAGA activity. At least the recombinant enzyme having an amino-acid sequence in which the 188th amino acid (serine) is replaced with glutamic acid and the 191st amino acid (alanine) is replaced with leucine is particularly preferable from the standpoint that the above-described effects can be satisfactorily achieved.

In addition, the protein of the present invention is preferably a protein described by (a) or (b):

(a) a protein containing any one of the amino-acid sequences described by (i) to (iii):

(i) an amino-acid sequence composed of the 18th amino acid to the 411th amino acid included in an amino-acid sequence in which the 188th amino acid is replaced with an amino acid other than serine in the amino-acid sequence shown in sequence No. 2;

(ii) an amino-acid sequence composed of the 18th amino acid to the 411th amino acid included in an amino-acid sequence in which the 191st amino acid is replaced with an amino acid other than alanine in the amino-acid sequence shown in sequence No. 2; and (iii) an amino-acid sequence composed of the 18th amino acid to the 411th amino acid included in an amino-acid sequence in which the 188th amino acid is replaced with an amino acid other than serine and the 191st amino acid is replaced with an amino acid other than alanine in the amino-acid sequence shown in sequence No. 2; or (b) a protein containing an amino-acid sequence in which one or several amino acids other than the amino acid or amino acids located at the replacement site or sites are deleted, replaced, or added in any one of the amino-acid sequences described by (i) to (iii), and having α-galactosidase activity.

The amino-acid sequence shown in sequence No. 2 is an amino-acid sequence composed of 411 amino acids constituting wild-type α-NAGA.

Specifically, the protein described by (a) is a protein composed of an amino-acid sequence containing an amino-acid sequence ranging from the 18th amino acid to the 411th amino acid excluding the 1st amino acid to the 17th amino acid, which constitute the signal peptide of wild-type α-NAGA, included in an amino-acid sequence in which at least one amino acid is replaced as described in (i) to (iii) in the amino-acid sequence shown in sequence No. 2. As described above, each of the 188th amino acid residue and the 191st amino acid residue is one of amino acids constituting the substrate-binding site.

Here, a preferable example of the amino-acid sequence containing an amino-acid sequence ranging from the 18th amino acid to the 411th amino acid is an amino-acid sequence in which a signal peptide is bound to the N-terminal of the amino-acid sequence ranging from the 18th amino acid to the 411th amino acid. The signal peptide is not limited as long as the signal peptide can allow the protein to pass through a cell membrane of an affected organ. For example, a signal peptide of a lysosomal enzyme such as wild-type α-NAGA or wild-type α-GAL, or a signal peptide of a secretase such as preprotrypsin is preferable. The signal peptide of wild-type α-NAGA or wild-type α-GAL is more preferable. The signal peptide of wild-type α-NAGA is a peptide composed of the 1st amino acid to the 17th amino acid included in the amino-acid sequence of wild-type α-NAGA shown in sequence No. 2. The signal peptide of wild-type α-GAL is a peptide composed of the 1st amino acid to the 31st amino acid included in the amino-acid sequence of wild-type α-GAL shown in sequence No. 13. The signal peptide of preprotrypsin is a peptide composed of the amino-acid sequence shown in sequence No. 15.

As the protein described by (a), among the proteins containing an amino-acid sequence described by (i), (ii), or (iii), a protein containing the amino-acid sequence described by (iii) is particularly preferable.

A preferable example of the protein described by (a) is a protein in which "the amino acid other than serine" described in (i) and (iii) is glutamic acid or aspartic acid. Similarly, another preferable example of the protein described by (a) is a protein in which "the amino acid other than alanine" described in (ii) and (iii) is one selected from the group consisting of leucine, valine, isoleucine, phenylalanine, and methionine.

Furthermore, a particularly preferable example of the protein described by (a) is a protein in which "the amino acid other than serine" described in (i) to (iii) is glutamic acid and "the amino acid other than alanine" described in (i) to (iii) is leucine. A preferable example of the protein is a protein (α-NAGA(S188E/A191L)) in which, in the amino-acid sequence of wild-type α-NAGA (sequence No. 2), the 188th serine is replaced with glutamic acid and the 191st alanine is replaced with leucine (refer to FIG. 7 and sequence No. 4). In general, regarding the alphabetical notation of amino acids, an amino acid is denoted by three letters (e.g., "Ser") or one letter (e.g., "S"). The letter of the alphabet located before a number (e.g., "188") representing the location of an amino acid from the N-terminal represents one-latter notation of an amino acid before replacement, and the letter of the alphabet located after the number represents one-letter notation of an amino acid after replacement. Accordingly, the notation "S188E" represents the case where the 188th Ser is replaced with Glu.

The protein described by (b) is not limited as long as the protein contains an amino-acid sequence in which one or several (for example, about one to ten, and preferably, about one to five) amino acids other than the amino acid or amino acids located at the replacement site or sites are deleted, replaced, or added in any one of amino-acid sequences described by (i) to (iii) included in the protein described by (a), and has α-galactosidase activity. Herein, the term "the replacement site" means, among the 394 amino acid residues constituting the amino-acid sequences described by (i) to (iii), the amino acid residue corresponding to the location of the 188th amino acid in the amino-acid sequence shown in sequence No. 2 (however, the amino-acid sequence being limited to the amino-acid sequence described by (i) or (iii)), and the amino acid residue corresponding to the location of the 191st amino acid in the amino-acid sequence shown in sequence No. 2 (however, the amino-acid sequence being limited to the amino-acid sequence described by (ii) or (iii)). More specifically, the former amino acid residue means the 171st amino acid residue in the amino-acid sequence described by (i) or (iii), and the latter amino acid residue means the 174th amino acid residue in the amino-acid sequence described by (ii) or (iii).

Note that it is important that the protein described by (b) is a protein that can stably exhibit α-GAL activity. Therefore, for example, amino acid residues which are believe to be important for binding performance (substrate-binding performance) with an α-galactose residue in a substrate of α-GAL and the catalytic reactivity to the substrate are preferably amino acid residues which are not mutated (deleted, replaced, or added) from the amino-acid sequences described by (i) to (iii). Preferable examples of the amino acid residues include, among the amino acid residues constituting the amino-acid sequences described by (i) to (iii), amino acid residues corresponding to the locations of the 28th to 31st amino acids, the 77th to 81st amino acids, the 117th to 127th amino acids, the 150th to 158th amino acids, the 192nd amino acid, the 209th to 220th amino acids, and the 242nd to 254th amino acids (in particular, the 156th and 217th aspartic acids (Asp: D)) in the amino-acid sequence shown in sequence No. 2.

Similarly, amino acid residues which are believed to be important for forming a homodimer are also preferably amino acid residues which are not mutated (deleted, replaced, or added) from the amino-acid sequences described by (i) to (iii). Preferable examples of the amino acid residues include, among the amino acid residues constituting the amino-acid sequences described by (i) to (iii), amino acid residues corresponding to the locations of the 45th amino acid and the 350th amino acid (specifically, the 45th aspartic acid (Asp: D) and the 350th arginine (Arg: R)) in the amino-acid sequence shown in sequence No. 2.

Furthermore, amino acid residues which are N-type-sugar-chain-binding sites are also preferably amino acid residues which are not mutated (deleted, replaced, or added) from the amino-acid sequences described by (i) to (iii). Preferable examples of the amino acid residues include, among the amino acid residues constituting the amino-acid sequences described by (i) to (iii), amino acid residues corresponding to the locations of the 124th, 177th, 201st, 359th, and 385th amino acids (all of which being asparagine (Asn: N)) in the amino-acid sequence shown in sequence No. 2.

In the present invention, α-GAL activity can be measured as follows. For example, a target protein is allowed to be expressed with a cell derived from mammals, such as a CHO cell or a human fibroblast, and is collected. The protein (enzyme solution) is then mixed with 4-methylumbelliferyl-α-D-galactoside (a synthetic substrate obtained from α-D-galactose and 4-methylumbelliferone (fluorogenic substrate)), and the mixture is allowed to react under an acidic condition. In this case, the amount of 4-methylumbelliferone released by a unit quantity of the enzyme solution per unit time is detected to measure α-GAL activity.

α-NAGA activity can also be measured as in α-GAL activity. A target protein is allowed to be expressed and is collected. The protein (enzyme solution) is then mixed with 4-methylumbelliferyl-α-N-acetyl-D-galactosaminide (a synthetic substrate obtained from α-N-acetyl-D-galactosamine and 4-methylumbelliferone (fluorogenic substrate)), and the mixture is allowed to react under an acidic condition. In this case, the amount of 4-methylumbelliferone which can be released per unit time by a unit quantity of the enzyme solution is detected to measure α-NAGA activity.

In the above methods of measuring α-GAL activity and α-NAGA activity, various types of known detection methods can be employed for detecting the fluorogenic substrate. For example, a detection method using a fluorophotometer or the like is preferable. The target protein can be expressed by incorporating a gene encoding the protein into a known expression vector or the like, and then introducing the vector into a cell. As the measurement methods, specifically, the methods described in Example 3 and Example 4 below can be preferably exemplified.

3. Recombinant Gene

Preferable examples of a gene encoding the above-described protein of the present invention include, but are not limited to, genes containing DNA described by (a) or (b) below. The DNAs described by (a) and (b) are preferably structural genes of the protein of the present invention. The gene containing any of these DNAs may entirely consist of the DNA. Alternatively, the gene may contain the DNA as a part thereof and may further contain other known base sequences (such as a transcriptional promoter, the SD sequence, the Kozak sequence, and a terminator) required for gene expression. Thus, the gene is not limited thereto.

(a) DNA containing any one of base sequences described by (i) to (iii);

(i) a base sequence composed of the 52nd to 1,236th bases included in a base sequence in which the 562nd to 564th bases "agc" are replaced with bases representing a codon of an amino acid other than serine in the base sequence shown in sequence No. 1;

(ii) a base sequence composed of the 52nd to 1,236th bases included in a base sequence in which the 571st to 573rd bases "gcc" are replaced with bases representing a codon of an amino acid other than alanine in the base sequence shown in sequence No. 1; and (iii) a base sequence composed of the 52nd to 1,236th bases included in a base sequence in which the 562nd to 564th bases "agc" are replaced with bases representing a codon of an amino acid other than serine and the 571st to 573rd bases are replaced with bases representing a codon of an amino acid other than alanine in the base sequence shown in sequence No. 1; or (b) DNA which encodes a protein having α-galactosidase activity and which hybridizes with DNA composed of a base sequence complementary to DNA containing any one of base sequences described by (i) to (iii) under a stringent condition, wherein bases corresponding to the bases at the replacement sites described above are identical to the bases at the replacement sites.

In the present invention, the term "codon" means not only the triple base linkage (triplet) of an RNA sequence after transcription but also the triple base linkage of a DNA sequence. Accordingly, codons of a DNA sequence are denoted using thymine (T) instead of uracil (U).

The base sequence shown in sequence No. 1 is a base sequence composed of 1,236 bases encoding wild-type α-NAGA.

More specifically, the DNA described by (a) is DNA composed of a base sequence containing a base sequence ranging from the 52nd base to the 1,236th base excluding the 1st base to the 51st base, which encode a signal peptide of wild-type α-NAGA, in a base sequence in which bases are replaced as described in (i) to (iii) in the base sequence shown in sequence No. 1.

Here, a preferable example of the base sequence containing a base sequence ranging from the 52nd base to the 1,236th base is a base sequence in which a base sequence (polynucleotide) encoding a signal peptide is bound to the 5' side of the base sequence ranging from the 52nd base to the 1,236th base. The signal peptide is not limited as long as the signal peptide can allow the protein to pass through a cell membrane of an affected organ. For example, a signal peptide of a lysosomal enzyme such as wild-type α-NAGA or wild-type α-GAL, or a signal peptide of a secretase such as preprotrypsin is preferable. A signal peptide of wild-type α-NAGA or wild-type α-GAL is more preferable. A base sequence encoding the signal peptide of wild-type α-NAGA is a base sequence composed of the 1st base to the 51st base in the base sequence of wild-type α-NAGA shown in sequence No. 1. A base sequence encoding the signal peptide of wild-type α-GAL is a base sequence composed of the 1st base to the 93rd base in the base sequence of wild-type α-GAL shown in sequence No. 12. A base sequence encoding the signal peptide of preprotrypsin is a base sequence shown in sequence No. 14.

As the DNA described by (a), among the DNAs containing the base sequence described by (i), (ii), or (iii), DNA containing the base sequence described by (iii) is particularly preferable.

In addition, as the DNA described by (a), DNA in which "the bases representing a codon of an amino acid other than serine" described in (i) and (iii) are bases representing a codon of glutamic acid or aspartic acid is preferable. Similarly, as the DNA described by (a), DNA in which "the bases representing a codon of an amino acid other than alanine" described in (ii) and (iii) are bases representing a codon of one selected from the group consisting of leucine, valine, isoleucine, phenylalanine, and methionine is also preferable. Herein, regarding bases representing a codon of each of the above amino acids (wherein the base disposed at the left end is defined as a base at the 5' side), bases representing a codon of glutamic acid are "gag" or "gaa" (preferably "gag"), and bases representing a codon of aspartic acid are "gat" or "gac". Similarly, bases representing a codon of leucine are "ctc", "ctt", "cta", or "ctg" (preferably "ctc"), bases representing a codon of valine are "gtt", "gtc", "gta", or "gtg", bases representing a codon of isoleucine are "att", "atc", or "ata", bases representing a codon of phenylalanine are "ttt" or "ttc", and bases representing a codon of methionine are "atg". Bases representing a codon of serine include "agt" in addition to "agc" mentioned above. Bases representing a codon of alanine include "gct", "gca", and "gcg" in addition to "gcc" mentioned above.

Furthermore, as the DNA described by (a) above, DNA in which "the bases representing a codon of an amino acid other than serine" described in (i) to (iii) are bases representing a codon of glutamic acid, and "the bases representing a codon of an amino acid other than alanine" described in (i) to (iii) are bases representing a codon of leucine is particularly preferable. A preferable example of such DNA is DNA composed of a base sequence (sequence No. 3) in which the 562nd to 564th bases, which are bases representing a codon of serine, included in the base sequence of wild-type α-NAGA (sequence No. 1) are replaced with bases representing a codon of glutamic acid ("agc"→"gag"), and the 571st to 573rd bases, which are bases representing a codon of alanine, included in the base sequence of wild-type α-NAGA (sequence No. 1) are replaced with bases representing a codon of leucine ("gcc"→"ctc"). In this exemplification, the 562nd to 564th bases after replacement are not limited to "gag" mentioned above and may be other bases as long as the bases represent a codon of glutamic acid. Similarly, the 571st to 573rd bases after replacement are not limited to "ctc" mentioned above and may be other bases as long as the bases represent a codon of leucine.

Such mutant DNA can be prepared in accordance with a site-directed mutagenesis method described in, for example, Molecular Cloning, A Laboratory Manual 2nd ed., Cold Spring Harbor Laboratory Press (1989), Current Protocols in Molecular Biology, John Wiley & Sons (1987-1997). Specifically, such DNA can be prepared by a known method such as a Kunkel method or a Gapped duplex method using a kit for introducing a mutation utilizing the site-directed mutagenesis method. Preferable examples of the kit include Quick-Change™ Site-Directed Mutagenesis Kit (manufactured by Stratagene), GeneTailor™ Site-Directed Mutagenesis System (manufactured by Invitrogen Corporation), and TaKaRa Site-Directed Mutagenesis System (e.g., Mutan-K or Mutan-Super Express Km: manufactured by Takara Bio Inc.).

Alternatively, as described in Examples below, such DNA can be prepared by performing a polymerase chain reaction (PCR) under an appropriate condition using a PCR primer which is designed such that a missense mutation is introduced to produce bases representing a codon of a desired amino acid, and using, as a template, for example, DNA containing a base sequence encoding wild-type α-NAGA. Preferable examples of such a PCR primer include synthetic oligonucleotide primers shown in sequence Nos. 8 and 10, which are described in Example 1 below. A DNA polymerase used for the PCR is not limited, but a DNA polymerase with high accuracy is preferable. Preferable examples thereof include Pwo DNA (Polymerase Roche Diagnostics K.K.), Pfu DNA polymerase (Promega), platinum Pfx DNA polymerase (Invitrogen Corporation), KOD DNA polymerase (Toyobo Co., Ltd.), and KOD-plus-polymerase (Toyobo Co., Ltd.). Reaction conditions for the PCR can be appropriately determined in accordance with, for example, the optimum temperature of DNA polymerase used, and the length and the type of DNA to be synthesized. For example, under preferable cycle conditions, a cycle consisting of "5 to 30 seconds at 90° C. to 98° C. (thermal denaturation and dissociation)→5 to 30 seconds at 50° C. to 65° C. (annealing)→30 to 1,200 seconds at 65° C. to 80° C. (synthesis and extension)" is performed a total of 20 to 200 times.

The DNA described by (b) can be obtained as follows. A known hybridization method such as colony hybridization, plaque hybridization, or Southern blotting is performed using DNA containing any one of base sequences described by (i) to (iii) (i.e., DNA described by (a)), DNA composed of a base sequence complementary to this DNA, or a fragment thereof as a probe, and the DNA described by (b) can be obtained from a cDNA library or a genomic library. A library prepared by a known method may be used. Alternatively, a commercially available cDNA library or genomic library may be used. The library is not limited thereto.

Regarding a detailed procedure of the hybridization method, refer to, for example, Molecular Cloning, A Laboratory Manual 2nd ed. (Cold Spring Harbor Laboratory Press (1989)) as needed.

The term "stringent condition" during the performance of a hybridization method means a condition during washing after hybridization, and specifically, a salt concentration of a buffer in the range of 15 to 330 mM and a temperature in the range of 25° C. to 65° C., and preferably, a salt concentration in the range of 15 to 150 mM and a temperature in the range of 45° C. to 55° C. More specifically, an example of the stringent condition is a salt concentration of 80 mM and a temperature of 50° C. Furthermore, in addition to the salt concentration, the temperature, and the like, in consideration of other conditions such as the probe concentration, the length of the probe, and the reaction time, conditions for obtaining the DNA described by (b) can be appropriately determined.

The DNA to be hybridized has a base sequence having a homology of preferably at least 40% or more, more preferably 60%, further preferably 90% or more, particularly preferably 95% or more, and most preferably 99% or more relative to the base sequence of the DNA described by (a).

Furthermore, in the DNA described by (b), bases corresponding to the bases at the replacement sites described above are the same as the bases at the replacement sites.

Herein, the term "replacement sites" means sites of the base replacements performed in any one of base sequences described by (i) to (iii) contained in the DNA described by (a). Specifically, the term "replacement sites" means sites of bases (triplet) representing a codon after the change caused by the base replacements. More specifically, the term "replacement sites" means, among 1,185 bases constituting the base sequences described by (i) to (iii), bases corresponding to the locations of the 562nd to 564th bases in the base sequence shown in sequence No. 1 (however, the base sequences being limited to the base sequences described by (i) and (iii)), and bases corresponding to the locations of the 571st to 573rd bases in the base sequence shown in sequence No. 1 (however, the base sequences being limited to the base sequences described by (ii) and (iii)). More specifically, the former bases mean the 511th to 513th bases in the base sequences described by (i) and (iii) above, and the latter bases mean the 520th to 522nd bases in the base sequences described by (ii) and (iii) above.

In addition, the term "bases corresponding . . . " in the phrase "bases corresponding to the bases at the replacement sites" means bases (triplet) which are located so as to face bases (triplet) complementary to the bases at the replacement sites in a hybrid prepared by hybridizing the DNA described by (b) with a strand complementary to the DNA described by (a). For example, when the base sequence of the DNA described by (b) does not have a mutation such as deletion or addition, as compared with the DNA described by (a) (that is, when the length (the number of bases) of the DNA described by (a) is the same as the length (the number of bases) of the DNA (b)), the 511th to 513th bases and/or the 520th to 522nd bases in the base sequence of the DNA described by (b) are the above "bases corresponding . . . " in the phrase "bases corresponding to the bases at the replacement sites".

It is important that the DNA described by (b) be DNA encoding a protein having α-GAL activity. Therefore, for example, bases representing a codon of an amino acid residue which is believed to be important for the binding performance (substrate-binding performance) with an α-galactose residue in a substrate of α-GAL and the catalytic reactivity to the substrate are preferably bases which are not mutated (deleted, replaced, or added) from the base sequences described by (i) to (iii). Preferable examples of such bases of the base sequences described by (i) to (iii) include bases corresponding to the locations of the 82nd to 93rd bases (4 codons), the 229th to 243rd bases (5 codons), the 349th to 381st bases (11 codons), the 448th to 474th bases (9 codons), the 574th to 576th bases (1 codon), the 625th to 660th bases (12 codons), and the 724th to 762nd bases (13 codons) in the base sequence shown in sequence No. 1 among the base sequences described by (i) to (iii). Among these bases, bases corresponding to the 466th to 468th bases and 649th to 651st bases, which represent codons of amino acid residues of a catalytic site, are particularly preferable.

Furthermore, in the DNA described by (b), bases representing a codon of an amino acid residue which is believed to be important for forming a homodimer are also preferably bases which are not mutated (deleted, replaced, or added) from the base sequences described by (i) to (iii). Preferable examples of such bases of the base sequences described by (i) to (iii) include bases corresponding to the locations of the 133rd to 135th bases and the 1,048th to 1,050th bases in the base sequence shown in sequence No. 1 among the base sequences described by (i) to (iii).

Furthermore, in the DNA described by (b), bases representing a codon of an amino acid residue which is an N-type-sugar-chain-binding site are also preferably bases which are not mutated (deleted, replaced, or added) from the base sequences described by (i) to (iii). Preferable examples of such bases of the base sequences described by (i) to (iii) include bases corresponding to the locations of the 370th to 372nd bases, the 529th to 531st bases, the 601st to 603rd bases, the 1,075th to 1,077th bases, and the 1,153rd to 1,155th bases in the base sequence shown in sequence No. 1 among the base sequences described by (i) to (iii).

A particularly preferable example of the DNA described by (b) is DNA composed of a base sequence which is not completely the same as the base sequence of the DNA described by (a) but in which the amino-acid sequence after translation is completely the same as the amino-acid sequence of the DNA described by (a) (i.e., DNA obtained by performing a silent mutation on the DNA described by (a)).

Regarding a gene encoding the protein of the present invention, codons corresponding to each of the amino acids after translation are not particularly limited. Accordingly, the gene encoding the protein of the present invention may contain DNA representing codons which are generally used (preferably, codons whose frequency of use is high) in mammals, such as the human, after transcription. Alternatively, the gene may contain DNA representing codons which are generally used (preferably, codons whose frequency of use is high) in, for example, a microorganism, such as *E. coli* or yeast, or a plant, after transcription.

4. Recombinant Vector and Transformant

In order to express the protein of the present invention, first, it is necessary to incorporate the above-described gene of the present invention into an expression vector to construct a recombinant vector. In this step, as needed, a transcriptional promoter, the SD sequence (in the case where a host is a prokaryotic cell), and the Kozak sequence (in the case where a host is a eukaryotic cell) may be linked upstream of the gene to be incorporated into the expression vector in advance. A terminator may be linked downstream thereof in advance. Furthermore, an enhancer, a splicing signal, a poly-A addition signal, a selective marker, and the like may also be linked in advance. The above elements, such as a transcriptional promoter, required for expressing a gene may be originally contained in the gene. In the case where these elements are originally contained in the expression vector, the elements contained in the expression vector may be utilized. Thus, the form of use of these elements is not particularly limited.

As a method of incorporating the gene into an expression vector, various types of methods using a known gene recombination technique, for example, a method using a restriction enzyme, or a method using a topoisomerase, can be employed. The expression vector is not limited as long as the expression vector can maintain a gene encoding a protein of the present invention. Examples of the expression vector include plasmid DNA, bacteriophage DNA, retrotransposon DNA, a retrovirus vector, and artificial chromosome DNA. A vector which can be suitably combined with a host cell used can be appropriately selected and used.

Subsequently, the constructed recombinant vector is introduced into a host to obtain a transformant, and the transformant is cultured. Thus, the protein of the present invention can be expressed. The term "transformant" used in the present invention means a product in which a foreign gene is introduced into a host. For example, the transformant includes a product in which a foreign gene is introduced by introducing plasmid DNA or the like into a host (transformation) and a product in which a foreign gene is introduced by infecting a host with a virus or a phage (transduction).

The host is not limited as long as the host can express a protein of the present invention after the recombinant vector is introduced thereinto, and can be appropriately selected. Examples thereof include known hosts such as animal cells, e.g., a human cell and a mouse cell, plant cells, bacteria, yeast, and plant cells.

When an animal cell is used as a host, for example, a human fibroblast, a CHO cell, a monkey COS-7 cell, Vero, a mouse L cell, a rat GH3, a human FL cell, or the like is used. Alternatively, insect cells such as an Sf9 cell or an Sf21 cell can also be used.

When a bacterium is used as a host, for example, *E. coli* or *Bacillus subtilis* is used.

When yeast is used as a host, for example, *Saccharomyces cerevisiae* or *Schizosaccharomyces pombe* is used.

When a plant cell is used as a host, for example, a tobacco BY-2 cell is used.

The method of obtaining a transformant is not limited and can be appropriately selected in consideration of the combination of the types of host and expression vector used. Preferable examples of the method include an electroporation method, a lipofection method, a heat shock method, a polyethylene glycol (PEG) method, a calcium phosphate method, a diethylaminoethyl dextran (DEAE-dextran) method, and a method of infecting a virus such as a DNA virus or an RNA virus.

In the resulting transformant, the codon type of a gene contained in the recombinant vector is not limited. The codon type may be identical to or different from the codon type of a host which is actually used.

5. Method of Producing Protein

A protein of the present invention can be produced by changing the structure of the active site (in particular, the substrate-binding site) of wild-type α-NAGA so that a substrate of α-GAL can be bound thereto. If the substrate of α-GAL can be bound to the active site, the substrate can be hydrolyzed by a catalysis due to the catalytic site of wild-type α-NAGA.

Such a structural change is performed as follows. For example, as described above, in the amino-acid sequence constituting the active site (substrate-binding site) of wild-type α-NAGA, (i) the 188th serine is replaced with another amino acid such as glutamic acid or aspartic acid, (ii) the 191st alanine is replaced with another amino acid such as leucine, valine, isoleucine, phenylalanine, or methionine, or (iii) both the 188th serine and the 191st alanine are replaced as described in (i) and (ii) above by a gene recombination technique. The structural change can be achieved by changing the three-dimensional structure of the side chains of the amino acids before and after the replacement. Consequently, the substrate specificity of wild-type α-NAGA can be changed. In particular, the above structural change is preferably performed by replacing the 188th serine with glutamic acid and by replacing the 191st alanine with leucine. Thereby, the substrate specificity of α-GAL can be imparted to α-NAGA. In the above structural change, an amino acid replacement which causes a significant three-dimensional structural change is the replacement of the 191st alanine with, for example, leucine. More specifically, the side chain of the 191st amino acid is changed from "—$CH_3$", which is the side chain of alanine, to a bulky side chain, such as "—$CH_2$—CH ($CH_3$)—$CH_3$", which is the side chain of leucine. As a result, the space of the active site in which the N-acetyl group in a substrate of α-NAGA is incorporated is restricted, thereby decreasing the binding performance of the protein with the substrate. Instead, the binding performance with a substrate of α-GAL is increased accordingly.

The protein of the present invention can be produced specifically by a method including a step of culturing the above-descried transformant and a step of collecting a protein having α-galactosidase activity from the resulting cultured product. Herein, the term "cultured product" means all of a culture supernatant, cultured cells, cultured bacteria, disrupted cells, and disrupted bacteria. The culture of the transformant can be performed in accordance with a normal method used for culturing a host. The target protein is accumulated in the cultured product.

As a medium used for the culture, a known natural medium or a synthetic medium may be used as long as the medium contains, for example, a carbon source, a nitrogen source, and inorganic salts, all of which can be utilized by the host, and the transformant can be cultured efficiently.

In order to prevent detachment of a recombinant vector contained in the transformant and detachment of a gene encoding a target protein, the culture may be performed in a state in which a selective pressure is applied. Specifically, in the case where a selective marker is a drug-resistance gene, a corresponding drug can be added to the medium. In the case where a selective marker is an auxotrophic complementary gene, a corresponding nutritional factor can be removed from the medium. For example, in the case where a human fibroblast transduced with a vector containing the G418-resistant gene is cultured, G418 (G418 sulfate) may be added during culturing, as needed.

In the case where, for example, a transformant transformed with an expression vector in which an inducible promoter is used as a promoter is cultured, an appropriate inducer (for example, isopropyl β-D-thiogalactopyranoside (IPTG)) may be added to the medium, as needed.

The culture conditions of the transformant are not particularly limited as long as productivity of the target protein and growth of the host are not interrupted. In general, the culture is performed at a temperature in the range of 10° C. to 40° C., and preferably in the range of 20° C. to 37° C. for 5 to 100 hours. The pH can be adjusted using an inorganic or organic acid, an alkaline solution, or the like. Examples of the method of culturing include solid culture, static culture, shaking culture, and aeration stirring culture.

When the target protein is produced in bacteria or in cells, the target protein can be collected by disrupting the bacteria or the cells. As a method of disrupting the bacteria or the cells, for example, a high-pressure treatment using a French press or a homogenizer, an ultrasonic treatment, a milling treatment using glass beads or the like, an enzyme treatment using lysozyme, cellulase, pectinase, or the like, a freeze-thawing treatment, a treatment with a hypotonic solution, or a bacteriolysis-inducing treatment using a phage can be employed. After the disruption, the disruption residue (which contains a fraction insoluble in a cell extract) of the bacteria or the cells can be removed, as needed. Examples of the method of removing the residue include centrifugal separation and filtration. Furthermore, the efficiency of the removal of residue can be increased using, for example, a flocculant or a filter aid, as needed. The supernatant obtained after the removal of residue is a fraction soluble in the cell extract, and can be used as a crude protein solution.

When the target protein is produced in bacteria or in cells, alternatively, the bacteria of the cells may be recovered by, for example, centrifugal separation or membrane separation, and thus, the protein can be used without disrupting the bacteria or the cells.

In contrast, when the target protein is produced outside bacteria or outside cells, the culture solution is used without further treatment, or the bacteria or the cells are removed by, for example, centrifugal separation or filtration. Subsequently, the target protein is collected from the cultured product by, for example, extraction by ammonium sulfate precipitation, as needed. Furthermore, according to need, the target protein may be isolated and purified by dialysis and chromatography (such as gel filtration, ion-exchange chromatography, or affinity chromatography).

The production yield of a protein obtained by culturing a transformant or the like can be determined by, for example, sodium dodecyl sulfate-polyacrylamide gel electrophoresis (SDS-PAGE) in terms of the units per culture solution, the units per wet weight or dry weight of bacteria, the units per protein in a crude enzyme solution, or the like.

In addition to the protein synthesis system using a transformant described above, a target protein can be produced using a cell-free protein synthesis system in which no living cells are used.

The cell-free protein synthesis system is a system in which a target protein is synthesized in an artificial container such as a test tube using a cell extract. A cell-free protein synthesis system which can be used also includes a cell-free transcription system in which RNA is synthesized using DNA as a template.

In this case, the cell extract used is preferably derived from the host cell described above. Examples of the cell extract that can be used include extracts derived from eukaryotic cells and extracts derived from prokaryotic cells. More specifically, examples of the cell extract include extracts of a CHO cell, a rabbit reticulocyte, a mouse L-cell, a HeLa cell, wheat germ, budding yeast, or *E. coli*. The cell extract may be concentrated or diluted for use. Alternatively, the cell extract may be used without further treatment. Thus, the method of using the cell extract is not limited.

The cell extract can be obtained by, for example, ultrafiltration, dialysis, and polyethylene glycol (PEG) precipitation.

Alternatively, such cell-free protein synthesis can be performed using a commercially available kit. Examples of the kit include a reagent kit PROTEIOS™ (Toyobo Co., Ltd.), TNT™ System (Promega), a synthesis device PG-Mate™ (Toyobo Co., Ltd.), and RTS (Roche Diagnostics K.K.).

The target protein produced by cell-free protein synthesis can be purified by appropriately selecting means such as chromatography, as described above.

6. Pharmaceutical Composition (i) Pharmaceutical Composition Used as Enzyme Agent Used in Enzyme Replacement or the like As described above, the protein of the present invention can achieve various excellent effects regarding the treatment of Fabry disease, and thus can be used as an active ingredient of a therapeutic agent for Fabry disease. That is, the present invention provides a therapeutic agent for Fabry disease containing a pharmaceutical composition containing the above-described protein of the present invention. A preferable specific example of this therapeutic agent is an enzyme agent that can be used for enzyme replacement therapy.

The protein of the present invention, which functions as an active ingredient in the pharmaceutical composition, may be used in the form of a salt, a hydrate, or the like, as needed. In addition, the protein of the present invention may be used in a state in which an appropriate chemical modification is performed in consideration of storage stability (in particular, maintenance of activity) as a therapeutic agent. Thus, the form of the protein of the present invention is not limited.

The pharmaceutical composition may contain components other than the protein of the present invention. Examples of the other components include pharmaceutical various components (such as various types of pharmaceutically acceptable carriers) that are required in accordance with the usage (the form of usage) of the pharmaceutical composition. The other components can be appropriately contained as long as the effects achieved by the protein of the present invention and the like are not impaired.

In the case where the pharmaceutical composition is used as an enzyme agent used in enzyme replacement, the mixing ratio of the protein of the present invention, and the types and mixing ratios of other components used can be appropriately determined in accordance with a preparation method of a known enzyme agent used in enzyme replacement (in particular, an enzyme agent used in enzyme replacement therapy for Fabry disease).

The method of administrating the pharmaceutical composition is not limited. When the pharmaceutical composition is an enzyme agent used in enzyme replacement, parenteral administration such as intravenous drip is generally used. In the pharmaceutical preparation that can be used in various administration methods such as parenteral administration, for example, an excipient, a filler, an extender, a binder, a humectant, a disintegrant, a lubricant, a surfactant, a dispersant, a buffer, a preservative, a solubilizer, an antiseptic, a flavoring agent, a soothing agent, a stabilizing agent, and an isotonizing agent, all of which are generally used in the production of medicine, may be appropriately selected and used, and thus, the pharmaceutical composition can be prepared by an existing method.

The form of the pharmaceutical composition is not limited. When the pharmaceutical composition is an enzyme agent used in enzyme replacement, an intravenous injection (including drip infusion) is generally used. For example, the pharmaceutical composition can be provided in the form of, for example, a single-dose ampule or a multi-dose container.

In general, the dosage of the pharmaceutical composition can be appropriately determined in a wide range in consideration of not only the mixing ratio of the active ingredient in the pharmaceutical preparation but also the age and body weight of the subject (patient) to be administered with the pharmaceutical composition, the type of disease, the state of disease, the administration route, the number of administrations, the term of administration, and the like. In particular, in the case where the therapeutic agent of the present invention is an enzyme agent used in enzyme replacement, the number of times of administration is preferably about one in every two to four weeks. In such a case, the amount of enzyme agent administered each time is determined such that, for example, preferably about 0.1 to 10 mg/kg, more preferably about 0.1 to 5 mg/kg, and further preferably about 0.2 to 1 mg/kg of the protein or the like (recombinant enzyme) of the present invention, which is an active ingredient, can be administered relative to the body weight of a patient.

In the present invention, the protein (recombinant enzyme) of the present invention, which functions as an active ingredient, has excellent stability in blood and high incorporation efficiency into a cell of an affected organ. Therefore, even when the protein is used in an amount smaller than that in known pharmaceutical compositions, the effect of enzyme replacement which is the same as or stronger than that achieved by the known pharmaceutical compositions can be achieved. In addition, allergic adverse side effects of the protein of the present invention are negligible. Accordingly, physical, mental, and economical burdens on patients can be markedly reduced.

(ii) Pharmaceutical Composition Used as Gene Therapeutic Agent

As described above, the gene of the present invention encodes a protein of the present invention which can achieve various excellent effects regarding the treatment of Fabry disease, and thus can be used as an active ingredient of a therapeutic agent (gene therapeutic agent) of Fabry disease. That is, the present invention provides a gene therapeutic agent for Fabry disease containing, as an active ingredient, a pharmaceutical composition containing the above-described gene of the present invention.

In the case where the pharmaceutical composition is used as a gene therapeutic agent, a method of directly administering by injection or a method of administering a vector into which a nucleic acid is incorporated is used. Examples of the vector include an adenovirus vector, an adeno-associated virus vector, a herpesvirus vector, a vaccinia virus vector, a retrovirus vector, and a lentivirus vector. By using these virus vectors, the gene therapeutic agent can be administered with high efficiency. A commercially available gene transfer kit (for example, product name: AdenoExpress, manufactured by Clontech) can also be used.

In addition, in the case where the pharmaceutical composition is used as a gene therapeutic agent, the composition may be introduced into a phospholipid endoplasmic reticulum such as liposome, and the endoplasmic reticulum may be administered. Specifically, an endoplasmic reticulum in which a gene of the present invention is held is introduced into a predetermined cell by a lipofection method. The resulting cell is then administered in, for example, a vein or an artery. Alternatively, such a cell can be locally administered in an organ affected by Fabry disease. For example, in the case where the pharmaceutical composition is administered to an adult, the dose is preferably about 0.1 µg/kg to 1,000 mg/kg, and more preferably, about 1 µg/kg to 100 mg/kg per day relative to the body weight of the patient.

7. Method of Treating Fabry Disease

The present invention includes a method of treating Fabry disease including administering the pharmaceutical composition to a Fabry patient. The present invention also includes the use of the pharmaceutical composition for treating Fabry disease, and the use of the pharmaceutical composition or the protein of the present invention for producing medicine for treating Fabry disease.

The pharmaceutical composition used in the method of treatment of the present invention may be a pharmaceutical composition containing a protein of the present invention ("section 6 (i)" above), a pharmaceutical composition containing a gene of the present invention ("section 6 (ii)" above), or a combination of these pharmaceutical compositions. The pharmaceutical composition is not limited thereto, and can be appropriately selected in consideration of the state of disease of the patient, the presence or absence of adverse side effects, the administration effect, and the like. Here, each of the pharmaceutical compositions to be administered to a Fabry patient can be administered in the form of usage of the enzyme agent used in enzyme replacement or the gene therapeutic agent described above.

In particular, when the pharmaceutical compositions are used in combination as described above, for example, the proportion of the amount of administration, the number of times of administration, and the term of administration of each of the pharmaceutical compositions can be appropriately determined in accordance with the conditions of each patient. For example, a preferable method of administration and a preferable amount of administration of each of the pharmaceutical compositions and the like are as described above.

The present invention will now be descried more specifically using Examples, but the present invention is not limited thereto.

Example 1

<Selection of Mutation Sites to be Introduced into α-N-acetylgalactosaminidase (α-NAGA)>

In order to design a novel enzyme in which the substrate specificity of human α-NAGA is modified into a substrate specificity similar to that of human α-GAL, sites (locations of an amino acid) of mutation to be introduced into human α-NAGA were determined by comparison and study using three-dimensional structural models of proteins. The procedure and results of the determination are specifically described below.

1. Used Data

The amino-acid sequence data of human α-NAGA and human α-GAL which are registered in Swiss-Prot as described below were used. The protein three-dimensional structural data of chicken α-NAGA and human α-GAL which are registered in Protein Data Bank (PDB) as described below were used.

(1) Amino-Acid Sequence Data

Used data base: Swiss-Prot (tw.expasy.org/uniprot/)

|  | entry name | accession number |
|---|---|---|
| Human α-NAGA | NAGAB_HUMAN | P17050 |
| Human α-GAL | AGAL_HUMAN | P06280 |

(2) Protein Three-Dimensional Structural Data

Used data base: Protein Data Bank (PDB) (www.rcsb.org/pdb/)

| PDB ID | |
|---|---|
| Chicken α-NAGA | 1KTC (refer to *1 below) |
| Human α-GAL | 1R47 (refer to *2 below) |

*1: Garman SC et al., Structure (Camb), 2002, 10(3): 425-34.
*2: Garman SC et al., J. Mol. Biol., 2004, 19; 337(2): 319-35.

2. Construction of Three-Dimensional Structural Model of Human α-NAGA

The construction of a three-dimensional structural model of human α-NAGA was performed on the basis of the three-dimensional structure of chicken α-NAGA using a homology modeling method, which is an existing method (refer to Sutcliffe M J et al., Prot. Eng., 1987, 1, 377-84; and Sutcliffe M J et al., Prot. Eng., 1987, 1, 385-92). The three-dimensional structure of chicken-derived α-NAGA (the complex with a substrate) registered in PDB was used as a template three-dimensional structure. The degree of matching (identity) of amino acids between human α-NAGA and chicken α-NAGA is 75%, which satisfies the condition (identity≥30%) for constructing a three-dimensional structural model by the homology modeling method. The construction of a three-dimensional structural model by the homology modeling method was performed using MODELLER, which is existing software (capable of being used by accessing MODELLER CBSU Web (cbsuapps.tc.cornell.edu/modeller.aspx)). Furthermore, a model of a complex with a substrate of human α-NAGA was constructed by fitting a substrate bound to chicken α-NAGA into the constructed three-dimensional structural model of human α-NAGA in accordance with the position of the substrate bound to chicken α-NAGA.

3. Comparison of Three-Dimensional Structures Contributing to Substrate Specificity of Human α-GAL and that of Human α-NAGA The three-dimensional structure of human α-NAGA is similar to that of human α-GAL, and catalytic domains of both human α-NAGA and human α-GAL have a $(\beta\alpha)_8$-barrel structure. Amino acid residues (catalytic residues) required for a catalytic action existing in the active site (including a catalytic site and a substrate-binding site) are localized at the C-terminal side of each strand of the $(\beta\alpha)_8$-barrel structure. In FIGS. 1 and 2, the three-dimensional structures of human α-NAGA and human α-GAL are shown by a ribbon model, and amino acid residues of the catalytic site and the substrate-binding site in each of the structures are shown by a stick model. In order to compare the positional relationships between a substrate and the residues of the catalytic site and the substrate-binding site in terms of three-dimensional structure, the three-dimensional structure of α-NAGA was superimposed on the three-dimensional structure of α-GAL by the superimposing method developed by Kabsch (refer to Kabsch W. et al., Acta Crystallogr; 1976: A32, 827-828; and Kabsch W. et al., Acta Crystallogr; 1978: A34, 922-923). Subsequently, in the human α-NAGA model, amino acid residues related to the binding of the substrate were selected by extracting amino acid residues adjacent to the substrate. The results are shown in Table 1. The right column of Table 1 shows 14 amino acid residues selected from human α-NAGA, and the left column of Table 1 shows amino acids in human α-GAL which positionally correspond to the 14 amino acid residues.

TABLE 1

| Human α-GAL | Human α-NAGA |
|---|---|
| Trp47 | Trp33 |
| Asp92 | Asp78 |
| Asp93 | Asp79 |
| Tyr134 | Tyr119 |
| Cys142 | Cys127 |
| Lys168 | Lys154 |
| Asp170 (*) | Asp156 (*) |
| Cys172 | Cys158 |
| Glu203 | Ser188 |
| Leu206 | Ala191 |
| Tyr207 | Tyr192 |
| Arg227 | Arg213 |
| Asp231 (*) | Asp217 (*) |
| Asp266 | Asp252 |

(*) catalytic residue

These amino acid residues were compared with each other by superimposing the three-dimensional structure of human α-NAGA on that of human α-GAL to detect residues that are identical to each other and residues that are different from each other. Thus, common points and points of difference in the amino-acid sequences of human α-GAL and human α-NAGA were cleared.

4. Common Points between Human α-GAL and Human α-NAGA

Figure 2C:
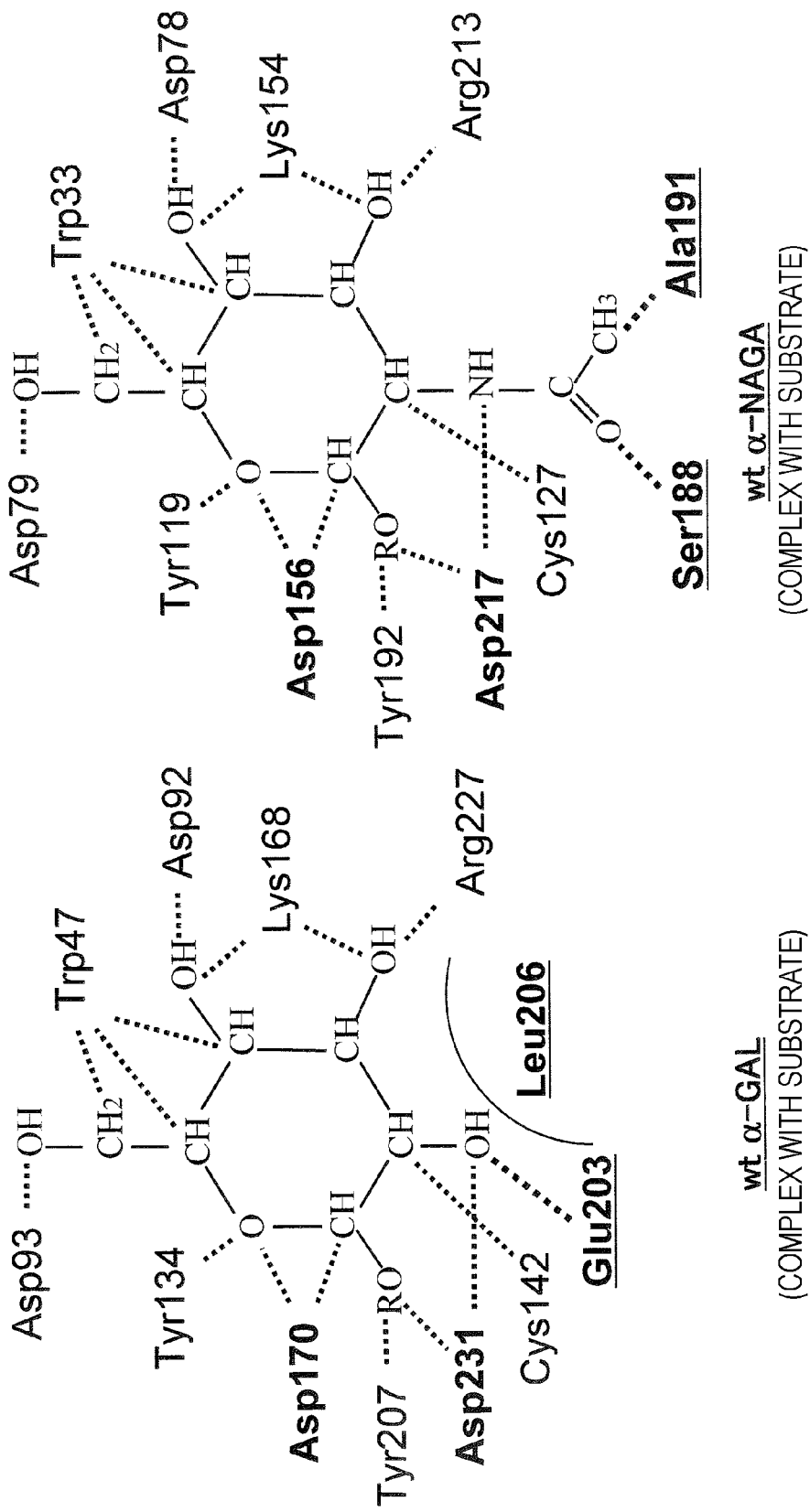
FIG. 2C includes schematic views showing amino acids constituting the active site of wild-type α-GAL and amino acids constituting the active site of wild-type α-NAGA, and interaction sites of the amino acids with a substrate.

As a result, it was found that among the 14 extracted residues, 12 residues including Asp156 and Asp217, which are the catalytic site of human α-NAGA, are identical between α-NAGA and α-GAL. Atoms in these amino acid residues in the superimposed three-dimensional structures are also satisfactorily superimposed with each other, and thus, it was confirmed that the locations in the three-dimensional structures are also very similar to each other. FIG. 2A shows locations of the amino acid residues in the three-dimensional structures, the amino acid residues being common to α-NAGA and α-GAL. FIG. 2C shows the interaction between each of the amino acid residues and a substrate. It is believed that all of these residues are related to the substrate by a hydrogen bond or a hydrophobic bond. Note that, in FIG. 2C, the amino acids which are not underlined are amino acids common to α-NAGA and α-GAL, and the underlined amino acids are amino acids different between α-NAGA and α-GAL.

5. Points of Difference between Human α-GAL and Human α-NAGA

There are two residues which are different between human α-GAL and human α-NAGA (refer to FIG. 2C). In α-GAL, the amino acid residues corresponding to Ser188 and Ala191 of α-NAGA were Glu203 and Leu206, respectively. FIG. 2B shows locations of the amino acid residues which are different between α-NAGA and α-GAL in the three-dimensional structure.

As shown in FIG. 2C, in α-GAL, an "—OH group (a hydroxyl group)" is bonded to the carbon atom at the 2-position of the sugar (six-membered ring) in the substrate of α-GAL, and in α-NAGA, an "—NH—C(CH$_3$)=O group (an N-acetyl group)" is boned to the carbon atom at the 2-position of the sugar (six-membered ring) in the substrate of α-NAGA.

It is supposed that, in α-NAGA, the hydroxyl group of the side chain of Ser188 is bonded to the oxygen atom of the N-acetyl group in the substrate by a hydrogen bond, and the methyl group of the side chain of Ala191 is bonded to the methyl group of the N-acetyl group in the substrate by a hydrophobic bond. On the basis of these suppositions, it was believed that Ser188 and Ala191 of α-NAGA are important residues for recognizing the N-acetyl group in the substrate.

In contrast, it has been reported that, in human α-GAL, Glu203 and Leu206, which are different from the corresponding residues of α-NAGA, are important for recognizing a substrate of α-GAL (Garman S C et al., J. Mol. Biol., 2004, 19; 337(2): 319-35). Furthermore, it has been cleared that, from X-ray crystal structure analysis, the carboxyl group of the side chain of Glu203 of α-GAL forms a hydrogen bond with the hydroxyl group of the substrate. In addition, Leu206 of α-GAL is a residue having a bulky side chain, and occupies a part of the space of the substrate-binding site of α-GAL. On the other hand, the hydroxyl group (at the 2-position) in the substrate of α-GAL is a functional group which is not bulky. It is obvious that the hydroxyl group is smaller than, for example, the N-acetyl group in the substrate of α-NAGA. Accordingly, it is believed that, in the binding between α-GAL and the substrate, the size of the space of the substrate-binding site of α-GAL is suitable for the size of the hydroxyl group in the substrate. Consequently, it was believed that, in α-GAL, two residues of Glu203 and Leu206 highly contribute to the substrate specificity.

6. Verification of Substrate Specificity by Three-Structural Models

Furthermore, in order to verify the interaction of α-NAGA with a substrate and the interaction of α-GAL with a substrate, models in which the substrates were exchanged with each other, that is, (i) a complex model combining the substrate of α-GAL with α-NAGA, and (ii) a complex model combining the substrate of α-NAGA with α-GAL, were constructed to examine the influence of the two residues which are different between α-NAGA and α-GAL on the substrates.

According to the results, in the complex model in which the substrate of α-GAL was fitted into the α-NAGA model structure, the side chain of Ser188 of α-NAGA did not interact with the hydroxyl group at the 2-position of the substrate of α-GAL. In addition, a clearance space was formed between Ala191 and the substrate of α-GAL, and thus, interaction with the hydroxyl group was not observed. On the other hand, in the complex model in which the substrate of α-NAGA was fitted into the α-GAL structure, it was confirmed that the N-acetyl group at the 2-position of the substrate of α-NAGA collides against Glu203 and Leu206 of α-GAL. Consequently, it was predicted that binding of the substrate was blocked by the presence of these two residues.

These predicted results supported the experimental results described above. Thus, it was supported that Ser188 and Ala191 of α-NAGA and Glu203 and Leu206 of α-GAL are important for the substrate specificity of α-NAGA and α-GAL, respectively.

7. Amino-Acid Residue Replacement for Modifying Substrate Specificity of Human α-NAGA to Substrate Specificity Similar to that of Human α-GAL As described above, between human α-GAL and human α-NAGA, the amino acid sequences are completely identical including the catalytic site except for the two residues which recognize the functional group bonded to the carbon atom at the 2-position of the sugar (six-membered ring) in each of the substrates. This indicates it is possible to retain the catalytic activity as is before replacement and to change only the substrate specificity from α-NAGA specific to α-GAL specific or vice versa by replacing these two residues which highly contribute to the substrate specificity. In order that the substrate specificity of human α-NAGA is changed and α-GAL activity is expressed by α-NAGA, an amino-acid replacement at these two positions is important. By replacing Ser188 of human α-NAGA with Glu, the recognition by a hydrogen bond with the N-acetyl group of the substrate of α-NAGA can be removed, and an interaction by a hydrogen bond to a hydroxyl group of the substrate of α-GAL can be introduced. Furthermore, by replacing Ala191 of human α-NAGA with Leu, the space in which an N-acetyl group is to be incorporated in the binding of a substrate of α-NAGA is occupied by the bulky side chain of Leu, and thus, the binding of the substrate is blocked by this steric hindrance. It was predicted that, in α-NAGA, the original recognition of a substrate of α-NAGA could be removed and a high specificity with a substrate of α-GAL could be provided by the above effects.

8. Evaluation of Human α-NAGA Amino-Acid Replacement Model

In the case where Ser188 of α-NAGA was replaced with Glu and Ala191 thereof was replaced with Leu, in order to confirm the effect on the peripheral three-dimensional structure, a mutant α-NAGA (α-NAGA S188E/A191L) model was constructed, and the three-dimensional structure of the mutant α-NAGA model was compared with that of wild α-NAGA. As a result, it was confirmed that the above replacements did not affect the three-dimensional structure composed of peripheral amino acid residues. Accordingly, it was supposed that the mutant α-NAGA in which these mutations were introduced into human α-NAGA can exist without problems in terms of the three-dimensional structure.

In addition, a complex model in which a substrate of α-GAL was fitted into the structure of the mutant α-NAGA was constructed. As a result, it was confirmed that the side chain of Glu188 of the mutant α-NAGA exists within a distance in which the side chain of Glu188 can form a hydrogen bond with the hydroxyl group at the 2-position of the substrate (refer to FIG. 6(b)). Furthermore, in a complex model in which a substrate of α-NAGA is fitted into the structure of the mutant α-NAGA, it was supposed that the N-acetyl group at the 2-position of the substrate causes a steric hindrance with the side chain of Leu191, and thus, the complex model has a structure to which the substrate cannot be bound.

According to the above results, it was expected that the mutant α-NAGA loses the specificity to the original substrate of α-NAGA and acquires a high specificity to the substrate of α-GAL (that is, the mutant α-NAGA substantially loses α-NAGA activity and acquires α-GAL activity).

Figure 7:
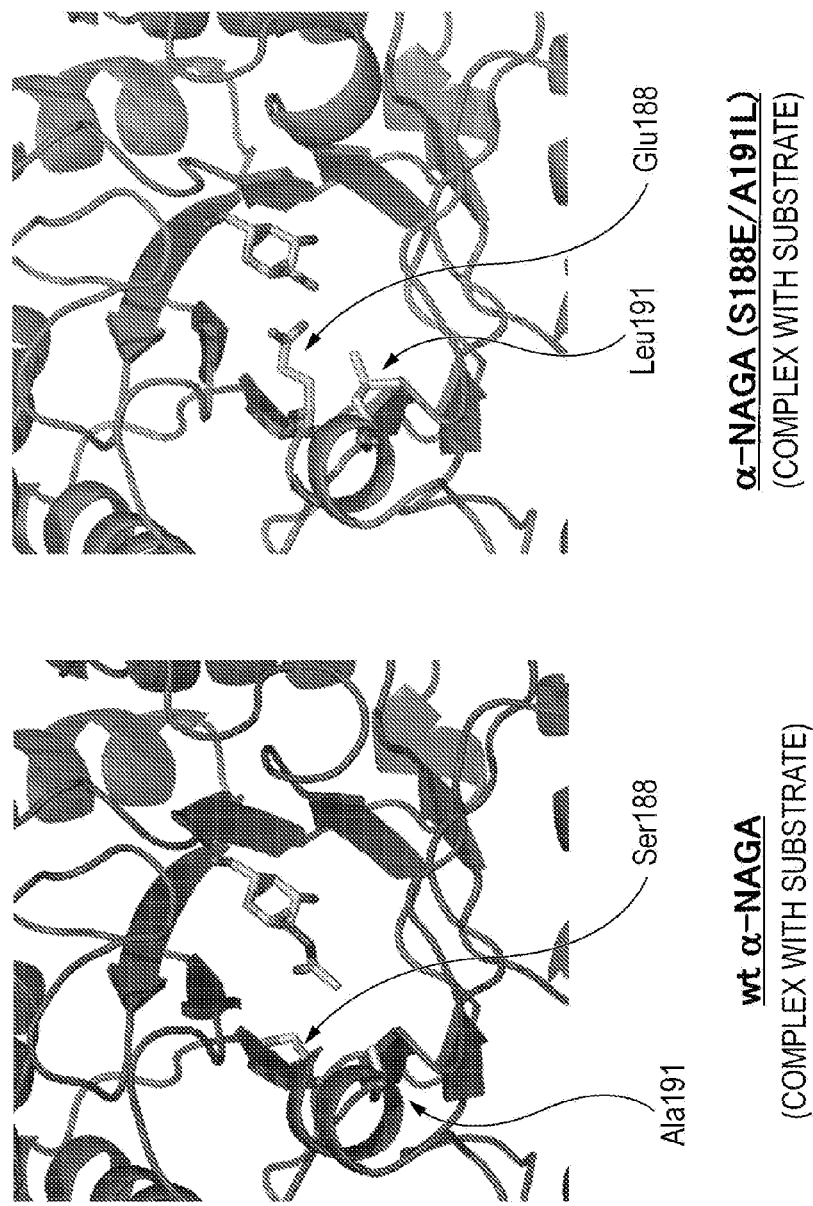
FIG. 7 includes schematic views showing the structures of the active site of wild-type α-NAGA and the active site of α-NAGA(S188E/A191L), which is an α-NAGA mutant.

The structure of the constructed mutant α-NAGA (α-NAGA S188E/A191L) is shown in FIG. 7.

9. Other Candidates of Human α-NAGA Amino-Acid Replacement

The above-described modification of the substrate specificity is achieved by two actions, i.e., a binding inhibition due to a steric hindrance to a substrate of α-NAGA and the formation of a hydrogen bond with a substrate of α-GAL. Furthermore, regarding the above-described amino-acid replacements, the presence or absence of the possibility of replacement to other amino acids was studied.

First, for the above action of the binding inhibition, a replacement with Leu, which is the same amino acid as that in α-GAL, was performed as a first candidate. Furthermore, as a replacement which achieved the same action, a replacement with Val, Ile, Phe, or Met, which is a hydrophobic amino-acid residue, was also possible.

In addition, for the above action of the formation of a hydrogen bond, a replacement with Glu, which is the same amino acid as that in α-GAL, was performed as a first candidate. Furthermore, as a replacement which achieved the same action, a replacement with Asp, which also has a carboxyl group as Glu, was also possible.

10. Amino-Acid Sequence of Wild-Type Human α-NAGA and Amino-Acid Sequence of Modified α-NAGA The amino-acid sequence of wild-type human α-NAGA is shown in "sequence No. 2", and the amino-acid sequence of the mutant α-NAGA (α-NAGA S188E/A191L) is shown in "sequence No. 4".

Example 2

1. Preparation of α-N-acetylgalactosaminidase (α-NAGA) Retrovirus Vector

An α-NAGA cDNA clone (Homo sapiens N-acetylgalactosaminidase, alpha, m-RNA, Gene Bank Accession: BC000095, IMAGE: 3504221) was purchased from Open Biosystems. The coding sequence of α-NAGA was amplified by PCR with a reaction mixture composition and under a reaction condition described below, using the purchased α-NAGA cDNA as a template with primers described below and KOD-plus-polymerase (Toyobo Co., Ltd.).

```
NAGA-5' primer:
                                    (sequence No. 5)
5'-GATGCTGCTGAAGACAGTGCTCTT-3'

NAGA-3' primer:
                                    (sequence No. 6)
5'-TCACTGCTGGGACATCTCCAGGTT-3'
```

<Reaction Mixture Composition>

| | |
|---|---|
| Template (10 ng/μL): | 1 μL |
| 10 × buffer: | 10 μL |
| 2.5 mM dNTP: | 10 μL |
| 25 mM MgSO$_4$: | 4 μL |
| KOD-plus-polymerase: | 1 μL |
| NAGA-5' primer (10 μM): | 1 μL |
| NAGA-3' primer (10 μM): | 1 μL |
| Sterilized water: | 68 μL |
| Total: | 100 μL |

<Reaction Condition>

The reaction mixture was heated at 94° C. for two minutes. Subsequently, a cycle consisting of "thermal denaturation and dissociation: 94° C. (15 seconds)→annealing: 60° C. (30 seconds)→synthesis and extension: 68° C. (90 seconds)" was performed a total of 35 times, and the reaction mixture was then cooled at 4° C.

The prepared α-NAGA DNA fragment was purified by agarose gel electrophoresis.

An α-NAGA DNA fragment whose ends were phosphorylated with T4 polynucleotide kinase (NEB) was ligated with a retrovirus vector pCX4Neo prepared by cleaving with a restriction enzyme Hpa I (Blant end) (NEB) and then dephosphorylating using Alkaline Phosphatase, Calf Intestine (NEB) (Tsuyoshi Akagi et al., Proc. Natl. Acad. Sci. USA, 100, 13567-13572 (2003)). α-NAGA pCX4Neo obtained by the ligation reaction was transformed into DH5α competent cells (Invitrogen Corporation) and seeded on an ampicillin-containing LB plate. Ampicillin-resistant colonies were then obtained.

The resulting each of the resistant colonies was suspended in an LB medium. A colony PCR was performed with a reaction mixture composition and under a reaction condition described below, using the bacterial suspension as a template with primers below and PCR Master Mix (manufactured by Promega).

```
NAGA-5' primer:
                              (sequence No. 5)
5'-GATGCTGCTGAAGACAGTGCTCTT-3' pCX4-3' primer
                              (sequence No. 7)
5'-AAACCGTTGCTAGCTTAAGTT-3'
```

<Reaction Mixture Composition>

| | |
|---|---|
| Template (1 colony/10 µL): | 1 µL |
| PCR Master Mix: | 10 µL |
| NAGA-5' primer (10 µM): | 0.5 µL |
| pCX4-3' primer (10 µM): | 0.5 µL |
| Sterilized water: | 8 µL |
| Total: | 20 µL |

<Reaction Condition>

The reaction mixture was heated at 95° C. for two minutes. Subsequently, a cycle consisting of "thermal denaturation and dissociation: 95° C. (30 seconds)→annealing: 55° C. (30 seconds)→synthesis and extension: 72° C. (90 seconds)" was performed a total of 40 times, and the reaction mixture was then cooled at 4° C.

A clone in which α-NAGA DNA was incorporated in the forward direction was selected from the resulting amplified product. More specifically, an *E. coli* template in which an amplified fragment of 1.4 kb was obtained was selected as a clone in which the α-NAGA DNA was incorporated in the forward direction. The selected *E. Coli* clone of α-NAGA pCX4Neo was cultured to obtain a large amount, i.e., 1 mg or more (1 mg/mL), of α-NAGA pCX4Neo plasmid DNA.

2. Preparation of α-NAGA Mutant

Regarding α-NAGA S188E/A191L, which is an α-NAGA mutant, first, α-NAGA S188E was prepared, and α-NAGA S188E/A191L was then prepared using α-NAGA S188E. α-NAGA S188E/A191L was prepared with reference to the instruction manual of the GeneTailor Site-Directed Mutagenesis System (Invitrogen Corporation), as needed.

First, α-NAGA pCX4Neo (100 ng) was methylated with DNA Methylase (4 U). α-NAGA S188E was prepared by amplifying the DNA with a reaction mixture composition and under a reaction condition described below, using the methylated α-NAGA pCX4Neo as a template with a NAGA S188E-GT-5' primer (a portion into which an S188E missense mutation was introduced being underlined) which was designed such that the missense mutation (S188E) in which the 188th serine (S) was replaced with glutamic acid (E) was introduced, a NAGA S188E-GT-3' primer, and KOD-plus-polymerase.

```
NAGA S188E-GT-5' primer:
                              (sequence No. 8)
5'-CCCATCGCCTTCTCCTGCGAGTGGCCAGCCTATGA-3'

NAGA S188E-GT-3' primer:
                              (sequence No. 9)
5'-GCAGGAGAAGGCGATGGGGCGGCCTGTG-3'
```

<Reaction Mixture Composition>

| | |
|---|---|
| Template (6 ng/µL): | 1 µL |
| 10 × buffer: | 5 µL |
| 2.5 mM dNTP: | 5 µL |
| 25 mM MgSO$_4$: | 2 µL |
| KOD-plus-polymerase: | 1 µL |
| NAGA S188E-GT-5' primer (10 µM): | 1 µL |
| NAGA S188E-GT-3' primer (10 µM): | 1 µL |
| Sterilized water: | 34 µL |
| Total: | 50 µL |

<Reaction Condition>

The reaction mixture was heated at 94° C. for two minutes. Subsequently, a cycle consisting of "thermal denaturation and dissociation: 94° C. (15 seconds)→annealing: 60° C. (30 seconds)→synthesis and extension: 68° C. (8 minutes)" was performed a total of 35 times, and the reaction mixture was then cooled at 4° C.

The amplified DNA fragment (α-NAGA S188E pCX4Neo) was transformed into DH5a-T1 competent cells (Invitrogen Corporation) having McrBC endonuclease which cleaves methylated DNA. Since α-NAGA pCX4Neo, which was used as a template, had been methylated, α-NAGA pCX4Neo was cleaved by McrBC endonuclease and could not form colonies. On the other hand, since a plasmid having an S188E mutation had not been methylated, the plasmid was not cleaved and could form colonies. The formed several colonies were then cultured, and the plasmid DNA was then extracted and purified. The introduction of the S188E mutation was confirmed by a known method of determining a base sequence using a sequencer.

Next, an α-NAGA S188E/A191L mutant was prepared by amplification by PCR with a reaction mixture composition and under a reaction condition described below, using the purified α-NAGA S188E pCX4Neo as a template with a NAGA A191L-GT-5' primer (a portion into which an A191L missense mutation was introduced being underlined) which was designed such that the missense mutation (A191L) in which the 191st alanine (A) was replaced with leucine (L) was introduced, a NAGA A191L-GT-3' primer, and KOD-plus-polymerase.

```
NAGA A191L-GT-5' primer:
                              (sequence No. 10)
5'-TTCTCCTGCGAGTGGCCACTCTATGAAGGCGGCCT-3'

NAGA A191L-GT-3' primer:
```

-continued (sequence No. 11)
5'-TGGCCACTCGCAGGAGAAGGCGATGGGG-3'

<Reaction Mixture Composition>

| | |
|---|---|
| Template (6 ng/μL): | 1 μL |
| 10 × buffer: | 5 μL |
| 2.5 mM dNTP: | 5 μL |
| 25 mM MgSO$_4$: | 2 μL |
| KOD-plus-polymerase: | 1 μL |
| NAGA A191L-GT-5' primer (10 μM): | 1 μL |
| NAGA A191L-GT-3' primer (10 μM): | 1 μL |
| Sterilized water: | 34 μL |
| Total: | 50 μL |

<Reaction Condition>

The reaction mixture was heated at 94° C. for two minutes. Subsequently, a cycle consisting of "thermal denaturation and dissociation: 94° C. (15 seconds)→annealing: 60° C. (30 seconds)→synthesis and extension: 68° C. (8 minutes)" was performed a total of 35 times, and the reaction mixture was then cooled at 4° C.

The amplified DNA fragment (α-NAGA S188E/A191L pCX4Neo) was transformed into DH5α-T1 competent cells. The plasmid DNA was then extracted and purified. The introduction of the A191L mutation in addition to the S188E mutation was confirmed by a known method of determining a base sequence using a sequencer.

3. Preparation of α-GAL-, α-NAGA-, and α-NAGA S188E/A191L-Expressing Recombinant Retroviruses Packaging cells of retrovirus (Phoenix Ampho Batch#: F-14727 Transformed Human Embryonic Kidney HEK293) were purchased from American Type Culture Collection (ATCC) (Coligan, J. E. et al., Curr. Protocols Immunol., Suppl. 31, 10.28.1-10.28.17 (1999)). The Phoenix Ampho cells were cultured in a Dulbecco's Modified Eagle Medium (DMEM) (High glucose)+10% heat-inactivated fetal bovine serum (FBS) culture solution at 37° C. and at a $CO_2$ concentration of 5%.

In order to prepare recombinant retroviruses, α-GAL pCX4Neo-, α-NAGA pCX4Neo-, or α-NAGA S188E/A191L pCX4Neo-retrovirus vector was transfected into the Phoenix Ampho cells. In this transfection, 2 mL of OPTI-MEM culture solution (Invitrogen Corporation) containing 1 μg of the retrovirus vector, 1 μg of pCLAMP (R K Naviaux et al., J. Virol., 70, 5701-5705 (1996)), and 18 μL of Dofect-GT1 (transfection reagent; Dojindo Laboratories) was added to the Phoenix Ampho cells (5×10$^5$/60-mm dish), and the mixture was incubated at 37° C. for four hours. Subsequently, the culture medium was changed to a normal culture medium, and the resulting mixture was cultured for 48 hours. After the culturing, the supernatant was collected and centrifuged at 1,000 rpm for 10 minutes. Recombinant retrovirus contained in the supernatant was dispensed and stocked at −80° C.

4. Establishment of Cell Strain which Stably Expresses Fabry Patient-Derived Fibroblasts (F377) which Express α-GAL-, α-NAGA-, or α-NAGA S188E/A191L Each of the α-GAL-, α-NAGA-, and α-NAGA S188E/A191L-expressing recombinant retroviruses prepared in section 3 above was infected in human fibroblasts (F377 cells) derived from a Fabry patient to establish stably expressing cells. Specifically, the establishment was achieved by performing the following steps (i) to (v):

(i) 1×10$^5$ F377 cells were seeded on a 60-mm dish and cultured at 37° C. for one night.

(ii) Polybrene (Sigma H-9266, Hexadimethrine Bromide) was added to the culture medium so that the final concentration of Polybrene was 2 μg/mL, and culturing was performed at 37° C. for 30 minutes.

(iii) The culture medium was removed. Subsequently, 1 mL of a virus solution was added and was adsorbed at 37° C. for 60 minutes.

(iv) The virus solution was removed. Subsequently, 5 mL of a culture medium was added, and culturing was performed for one night.

(v) Culturing was performed with a selective medium in which G418 (250 μg/mL) was added to a culture medium. Thus, G418-resistant F377 cells were established. The selective medium was changed once every three days for 14 days or more. Whether or not the established cell expressed the target protein was confirmed by the enzyme activity and a Western blotting method (section 5 below).

5. Confirmation of Expression of Target Protein by Western Blotting Method

In order to examine whether or not the α-NAGA- or α-NAGA S188E/A191L-expressing F377 cells which were established using retrovirus expressed the target protein, Western blotting was performed. An anti-α-NAGA polyclonal antibody obtained by a known method of preparing an antibody was prepared as an antibody used in this Western blotting.

Samples for the Western blotting were prepared as follows. α-NAGA- or α-NAGA S188E/A191L-expressing F377 cells cultured in a 60-mm dish were temporarily recovered, and resuspended in a Triton-X lysis buffer (50 mM Tris-HCl pH 7.4, 150 mM NaCl, and 1% Triton-X). The suspension was then subjected to an ultrasonic treatment, and centrifuged at 12,000 rpm for five minutes. The supernatant was recovered and used as a sample. SDS-PAGE was performed as follows. The concentration of a protein of the sample was measured. Subsequently, an equivalent volume of 2× SDS sample buffer (62.5 mM Tris-HCl pH 6.8, 4% SDS, 30% glycerol, and 0.2% bromophenol blue (BPB)) was added to the sample containing 5 μg of the protein. The mixture was boiled for five minutes, and the resulting sample was then applied to a 4% to 20% gel (PAG mini: Daiichi Pure Chemicals Co., Ltd.). Electrophoresis was performed at a constant current of 30 mA for two hours.

After the electrophoresis, in order to transfer the protein to a polyvinyl difluoride (PVDF) membrane (Immobilon-P, MILLIPORE), the gel was immersed in a blotting buffer (25 mM Tris-HCl pH 8.3, 192 mM glycan, and 20% methanol) for 20 minutes, and placed on a PVDF membrane equilibrated with the blotting buffer. Transfer was then performed using a Hoefer TE 70 semi-dry transfer unit (Amersham Biosciences) at a constant current of 60 mA for one hour.

After the completion of transfer, the membrane was blocked with a blocking buffer (5% skim milk in Tris-Buffered Saline (TBS) (50 mM Tris-HCl pH 7.4 and 100 mM NaCl)) for 30 minutes. An anti-NAGA polyclonal antibody (primary antibody) diluted by 500 times with the blocking buffer was then added thereto, and incubation was performed at 4° C. for one night.

The membrane obtained after the incubation with the primary antibody was washed with TBS for five minutes. This washing was performed three times. An anti-rabbit IgG HRP labeled antibody (secondary antibody; Amersham Biosciences) diluted by 5,000 times with the blocking buffer was then added thereto, and incubation was performed at room temperature for one hour.

The membrane obtained after the incubation with the secondary antibody was washed with TBS for five minutes. This washing was performed three times. An enhanced chemiluminescence (ECL) coloring reagent (Nacalai Tesque, Inc.) was added thereto, and reaction was performed at room temperature for two minutes. Subsequently, the membrane was developed by bringing into contact with Hyperfilm™ ECL in a darkroom for one minute.

According to the results, it was confirmed that the established α-NAGA-expressing F377 cells and α-NAGA S188E/A191L-expressing F377 cells expressed wild-type α-NAGA with a molecular weight of about 45 kD and a mutant α-NAGA (α-NAGA S188E/A191L), respectively.

Example 3

<Transition of Enzyme Activity of α-NAGA Mutant>

The fact that the mutant α-NAGA (α-NAGA S188E/A191L) had acquired the substrate specificity of α-GAL was confirmed by the following procedure.

First, a gene of wild-type α-NAGA or a gene of α-NAGA S188E/A191L was introduced into fibroblasts (F377) derived from a Fabry patient, and α-GAL activity and α-NAGA activity were measured. F377 cells were used as a negative control of α-GAL activity, and fibroblasts (F652) derived from a patient with Kanzaki disease (α-NAGA deficiency) were used as a negative control of α-NAGA activity. In addition, fibroblasts (F592) derived from a normal subject were used as a positive control of endogenous α-GAL activity and α-NAGA activity.

The cells cultured in a 60-mm dish were recovered and resuspended in Milli-Q water. The suspension was then subjected to an ultrasonic treatment to prepare a cell homogenate. This homogenate was used as a sample of an enzyme solution. The enzyme activity was determined using a synthetic substrate composed of a 4-methylumbelliferone (4-MU) derivative, which is a fluorogenic substrate, by measuring the amount of 4-MU released by 1 mL of the enzyme solution per hour as a fluorescence intensity. More specifically, 4-MU-α-D-galactoside (4-MU-α-GAL; Calbiochem, Calif.) was used as the synthetic substrate of α-GAL. 4-MU-α-N-acetyl-D-galactosaminide (4-MU-α-NAGA; Moscerdam Substrates, Rotterdam) was used as the synthetic substrate of α-NAGA. In the measurement of α-GAL activity, as an inhibitor of α-NAGA, which reacts with 4-MU-α-GAL at the same time, N-acetyl-D-galactosamine (Sigma, MO) was added to the substrate solution in advance so that the final concentration thereof was 117 mM.

A McIlvain's buffer (citric acid/phosphoric acid, pH 4.6, 60 μL) containing 5 mM 4-MU-α-GAL or a McIlvain's buffer (citric acid/phosphoric acid, pH 4.7, 40 μL) containing 1 mM 4-MU-α-NAGA was added to an enzyme solution (10 μL) and mixed, and a reaction was performed at 37° C. for 30 minutes. The reaction was terminated by adding a 0.2 M Glycine buffer (pH 10.7, 700 μL). In order to detect the amount of 4-MU released, the amount of 4-MU was measured at an excitation wavelength of 365 nm and at a fluorescence wavelength of 450 nm using a spectrofluorophotometer. The specific activity of α-GAL or α-NAGA was determined by dividing by the protein concentration (mg/mL) of the enzyme solution. The specific activity was defined as an enzyme activity in cell.

According to the results of the measurement of the enzyme activity, α-NAGA S188E/A191L, which had been subjected to a double mutation of S188E/A191L, exhibited high α-GAL activity. This result showed that α-NAGA S188E/A191L acquired the substrate specificity of α-GAL.

The results are shown in Table 2.

TABLE 2

Transition of enzyme activity of α-NAGA mutant

| transfection | mutation | α-GAL activity | α-NAGA activity |
|---|---|---|---|
| F592 Normal control | — | — | 112 | 252 |
| F652 Kanzaki disease | — | — | 40 | 0 |
| F377 Fabry disease | — | — | 2 | 233 |
| | α-NAGA | wild-type | 13 | 1295 |
| | α-NAGA | S188E/A191L | 552 | 105 |

(nmol/hr/mg protein)

Example 4

<Stability of α-NAGA Mutant in Blood (in Plasma)>

The stability of the α-NAGA mutant in blood (in plasma) was confirmed by a procedure below.

First, an enzyme solution of α-NAGA S188E/A191L was prepared as in Example 3. In addition, as a control, another enzyme solution was prepared in the same manner as the above enzyme solution using cells prepared by introducing a gene of wild-type α-GAL into F377. Plasma (50 μL) of a normal subject was added to each of the enzyme solutions (50 μL) and mixed. A reaction was then started at 37° C., and 10 μL of the reaction mixture was sampled at intervals to measure α-GAL activity. The enzyme activity was measured as in Example 3. The α-GAL activity of a sample sampled at the time of mixing of the enzyme solution with plasma was defined as the standard (100%), and a decrease in the enzyme activity with time was represented as a percentage.

According to the results, α-NAGA S188E/A191L had an excellent α-GAL-activity-maintaining ability with time in blood (in plasma), as compared with wild-type α-GAL. This result showed that α-NAGA S188E/A191L had a high stability in blood.

Figure 5:
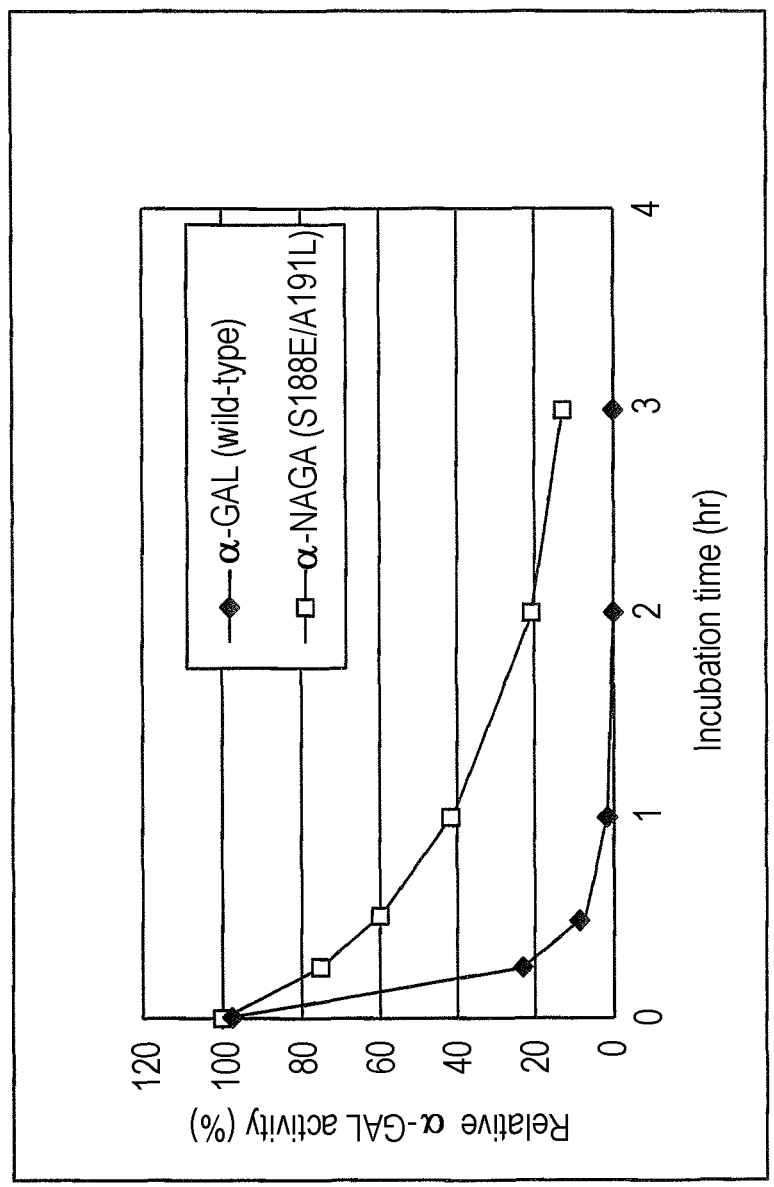
FIG. 5 is a graph showing the results obtained by comparing the stability of α-GAL in blood to that of an α-NAGA mutant with time on the basis of the residual ratio of α-GAL activity.

The results are shown in Table 3. In addition, plots of the results are shown in FIG. 5.

TABLE 3

Tests of stability of α-NAGA mutant in blood

| Incubation time | Relative α-GAL activity (%) | |
|---|---|---|
| (hr) | α-GAL(wild-type) | α-NAGA (S188E/A191L) |
| 0 | 100 | 100 |
| 0.25 | 23 | 75 |
| 0.5 | 7 | 60 |
| 1 | 2 | 42 |
| 2 | 0 | 21 |
| 3 | 0 | 13 |

INDUSTRIAL APPLICABILITY

According to the present invention, a protein which has α-galactosidase activity and which is advantageous in that no allergic adverse side effect is shown, the stability in blood is high, and the protein can be easily incorporated into a cell of an affected organ can be provided. This protein is very useful as excellent novel highly functional enzyme for the therapy for Fabry disease.

In addition, the present invention provides a gene which can encode the above protein, a recombinant vector containing the gene, a transformant or transductant containing the recombinant vector, and a method of producing the protein. Furthermore, a therapeutic agent for Fabry disease containing the protein can be provided.

SEQUENCE LISTING FREE TEXT

Sequence No. 3: recombinant DNA
Sequence No. 4: recombinant protein

Sequence No. 5: synthetic DNA
Sequence No. 6: synthetic DNA
Sequence No. 7: synthetic DNA
Sequence No. 8: synthetic DNA
Sequence No. 9: synthetic DNA
Sequence No. 10: synthetic DNA
Sequence No. 11: synthetic DNA

The invention claimed is:

1. An isolated protein comprising an amino-acid sequence of (a) or (b) below:
   (a) the amino-acid sequence comprising the 18th amino acid to 411st amino acid of the amino-acid sequence of SEQ ID NO:2, except that the 188th amino acid is substituted with glutamic acid or aspartic acid and the 191st amino acid is substituted with leucine, valine or isoleucine,
   wherein said isolated protein comprising the amino-acid sequence (a) has α-galactosidase activity; or
   (b) the amino-acid sequence comprising the 18th amino acid to 411st amino acid of the amino-acid sequence of SEQ ID NO:2, except that the 188th amino acid is substituted with glutamic acid or aspartic acid and the 191st amino acid is substituted with leucine, valine or isoleucine,
   wherein, in the amino-acid sequence (b), one to ten amino acids other than the 188th amino acid and the 191st amino acid are deleted, replaced or added,
   wherein said isolated protein comprising the amino-acid sequence (b) has α-galactosidase activity, and
   wherein in the amino-acid sequence (b), at least one of the following is not deleted, replaced or added:
   the amino acid at the 45th position, and
   the amino acid at the 350th position.

2. The isolated protein according to claim 1, wherein the 188th amino acid is substituted with glutamic acid, and the 191st amino acid is substituted with leucine.

3. A pharmaceutical composition comprising the protein according to claim 1.

4. A therapeutic agent for Fabry disease comprising the composition according to claim 3 as an active ingredient.

5. A method of treating Fabry disease, wherein the pharmaceutical composition according to claim 3 is administered to a Fabry patient.

6. The isolated protein according to claim 1, wherein one to five amino acids other than the 188th amino acid and the 191st amino acid are deleted, replaced or added.

* * * * *